United States Patent
Aoki et al.

(10) Patent No.: US 8,271,015 B2
(45) Date of Patent: Sep. 18, 2012

(54) BIOLOGICAL SAMPLE MEASUREMENT APPARATUS AND BIOLOGICAL SAMPLE MEASUREMENT SYSTEM EQUIPPED WITH SAME

(75) Inventors: Tooru Aoki, Ehime (JP); Eiji Okuda, Ehime (JP); Akiyoshi Oozawa, Ehime (JP); Hiroshi Ando, Ehime (JP); Kazuo Manabe, Ehime (JP); Norio Imai, Ehime (JP)

(73) Assignee: Panasonic Corporation, Osaka (JP)

( * ) Notice: Subject to any disclaimer, the term of this patent is extended or adjusted under 35 U.S.C. 154(b) by 513 days.

(21) Appl. No.: 12/600,582

(22) PCT Filed: Dec. 12, 2008

(86) PCT No.: PCT/JP2008/003756
§ 371 (c)(1),
(2), (4) Date: Nov. 17, 2009

(87) PCT Pub. No.: WO2009/081538
PCT Pub. Date: Jul. 2, 2009

(65) Prior Publication Data
US 2010/0159835 A1 Jun. 24, 2010

(30) Foreign Application Priority Data

Dec. 26, 2007 (JP) ................. 2007-333786
Jan. 25, 2008 (JP) ................. 2008-015641
Jan. 25, 2008 (JP) ................. 2008-015642
Jan. 25, 2008 (JP) ................. 2008-015643

(51) Int. Cl.
*H04Q 7/20* (2006.01)

(52) U.S. Cl. .......... 455/522; 455/69; 455/500; 455/423; 455/426.1; 455/414.1; 340/539.1; 340/539.11; 340/539.12; 600/508; 600/509; 600/510

(58) Field of Classification Search .............. 455/522, 455/69, 500, 517, 575.1, 127.1, 423–425, 455/67.11, 414.1–414.4, 426.1, 426.2, 403, 455/422.1, 550.1; 340/539.1, 539.11, 539.12; 600/508–510
See application file for complete search history.

(56) References Cited

U.S. PATENT DOCUMENTS
7,248,894 B2   7/2007   Fujieda et al.
(Continued)

FOREIGN PATENT DOCUMENTS
JP        5-41683        2/1993
(Continued)

OTHER PUBLICATIONS
International Search Report issued Feb. 3, 2009 in International (PCT) Application No. PCT/JP2008/003756.

*Primary Examiner* — Keith Ferguson
(74) *Attorney, Agent, or Firm* — Wenderoth, Lind & Ponack, L.L.P.

(57) ABSTRACT

A wireless blood glucose meter (2) has a blood glucose level detector (21), a transmitter (22), a receiver (23), a storage component (24), and a transmission power determiner (25). Whether or not an acknowledge signal has been received and the transmission power when the transmitter (22) has transmitted a blood glucose level are stored as history information in the storage component (24), and the transmission power determiner (25) determines the transmission power when the transmitter (22) transmits on the basis of the history information stored in the storage component (24).

25 Claims, 20 Drawing Sheets

U.S. PATENT DOCUMENTS

| | | |
|---|---|---|
| 2003/0236100 A1 | 12/2003 | Fujieda et al. |
| 2004/0185821 A1 | 9/2004 | Yuasa |
| 2006/0036134 A1 | 2/2006 | Tarassenko et al. |
| 2007/0149235 A1 | 6/2007 | Chin et al. |
| 2008/0045161 A1* | 2/2008 | Lee et al. ............ 455/73 |
| 2009/0226891 A2* | 9/2009 | Nova et al. ............ 435/6 |

FOREIGN PATENT DOCUMENTS

| | | |
|---|---|---|
| JP | 10-079776 | 3/1998 |
| JP | 10-285109 | 10/1998 |
| JP | 2000-188775 | 7/2000 |
| JP | 2002-142014 | 5/2002 |
| JP | 2002-251461 | 9/2002 |
| JP | 2003-309495 | 10/2003 |
| JP | 2004-266452 | 9/2004 |
| JP | 2005-136749 | 5/2005 |
| JP | 2005-538794 | 12/2005 |
| JP | 2006-148484 | 6/2006 |
| JP | 2006-165742 | 6/2006 |
| JP | 2006-340952 | 12/2006 |
| JP | 2007-188 | 1/2007 |
| JP | 2007-13538 | 1/2007 |
| JP | 2007075372 A * | 3/2007 |
| JP | 2007-142520 | 6/2007 |
| JP | 2009-521878 | 6/2009 |
| WO | 2007/120338 | 10/2007 |

* cited by examiner

| | MSB | LSB |
|---|---|---|
| DATA0 | day of week | transmission time |
| | ACK | transmission power |
| | blood glucose level (MSB) | |
| | blood glucose level (LSB) | |
| DATA1 | day of week | transmission time |
| | ACK | transmission power |
| | blood glucose level (MSB) | |
| | blood glucose level (LSB) | |

⋮

| | | |
|---|---|---|
| DATA254 | day of week | transmission time |
| | ACK | transmission power |
| | blood glucose level (MSB) | |
| | blood glucose level (LSB) | |
| DATA255 | day of week | transmission time |
| | ACK | transmission power |
| | blood glucose level (MSB) | |
| | blood glucose level (LSB) | |

FIG. 8

|  | MSB | LSB |
|---|---|---|
| DATA0 | day of week | transmission time |
| | ACK | transmission power |
| | noise power ||
| | blood glucose level (MSB) ||
| | blood glucose level (LSB) ||
| DATA1 | day of week | transmission time |
| | ACK | transmission power |
| | noise power ||
| | blood glucose level (MSB) ||
| | blood glucose level (LSB) ||

⋮

|  |  |  |
|---|---|---|
| DATA254 | day of week | transmission time |
| | ACK | transmission power |
| | noise power ||
| | blood glucose level (MSB) ||
| | blood glucose level (LSB) ||
| DATA255 | day of week | transmission time |
| | ACK | transmission power |
| | noise power ||
| | blood glucose level (MSB) ||
| | blood glucose level (LSB) ||

FIG. 15

|       | MSB | LSB |
|-------|-----|-----|
| DATA0 | day of week | transmission time |
| | transmission power | |
| | ACK | reception power |
| | reference reception power | |
| | blood glucose level (MSB) | |
| | blood glucose level (LSB) | |
| DATA1 | day of week | transmission time |
| | transmission power | |
| | ACK | reception power |
| | reference reception power | |
| | blood glucose level (MSB) | |
| | blood glucose level (LSB) | |

| | MSB | LSB |
|---|---|---|
| DATA255 | day of week | transmission time |
| | transmission power | |
| | ACK | reception power |
| | reference reception power | |
| | blood glucose level (MSB) | |
| | blood glucose level (LSB) | |

FIG. 18

BIOLOGICAL SAMPLE MEASUREMENT APPARATUS AND BIOLOGICAL SAMPLE MEASUREMENT SYSTEM EQUIPPED WITH SAME

TECHNICAL FIELD

The present invention relates to a biological sample measurement apparatus, and more specifically, relates to a biological sample measurement apparatus having a wireless communication function, and to a biological sample measurement system equipped with this.

BACKGROUND ART

With a conventional wireless portable terminal device, communication was performed with the wireless transmission power fixed at a constant level. However, when the transmission power is fixed, communication will be carried out at transmission power that is higher than necessary even at a distance at which communication is fully possible, which ends up wasting power consumption.

In light of this, wireless portable terminal devices have been disclosed in which the transmission power is optimally adjusted.

For example, as shown in FIG. 18, in Patent Citation 1, a reception power RX that is the power of the signal received by the communication partner device in a communication state is compared with a reference power RXref that is a reference for the reception power, and if RX is not greater than RXref, the transmission power is returned to its default value, but if RX is greater than RXref, the transmission power is reduced before data is transmitted. Here, if the error rate of reception data of the communication partner device has decreased, the transmission power is returned to its original value, but if the error rate has not decreased, the transmission power is controlled by maintaining the current transmission power.

Patent Citation 1: Japanese Laid-Open Patent Application H10-285109 (disclosed on 23 Oct. 1998)

DISCLOSURE OF INVENTION

Technical Problem

However, the following problems were encountered with the above-mentioned conventional wireless terminal device.

With the conventional wireless terminal device, since the transmission power is optimized on the basis of the error rate, optimization of the transmission power cannot be achieved until a specific volume of data is sent or received. Therefore, the transmission power cannot be optimized if an extremely small quantity of data is sent wirelessly, such as blood glucose level data measured with a wireless blood glucose meter, for example.

It is an object of the present invention to provide a biological sample measurement apparatus with which transmission power can be optimized regardless of the volume of data being transmitted, as well as a biological sample measurement system equipped with this apparatus.

Technical Solution

The biological sample measurement apparatus pertaining to the first invention is a biological sample measurement apparatus for communicating wirelessly with an external device, comprising a biological data measurement component, a transmitter, a receiver, a storage component, and a transmission power determiner. The biological data measurement component measures biological data. The transmitter transmits the biological data measured by the biological data measurement component. The receiver receives an acknowledge signal that is returned when the external device has properly received the biological data transmitted by the transmitter. The storage component stores as history information whether or not the acknowledge signal was received and a transmission power when the transmitter transmitted the biological data. The transmission power determiner determines transmission power of the transmitter on the basis of the history information stored in the storage component, or the history information extracted according to transmission power determination rule that sets forth extraction conditions.

Here, whether or not an acknowledge signal was received and the transmission power when the transmitter transmitted the biological data are stored as history information in the storage component. The transmission power determiner determines the transmission power when the transmitter transmits on the basis of the history information stored in the storage component, or history information extracted according to a transmission power determination rule that sets forth extraction conditions.

For example, when a portable terminal (a type of external device) has properly received a blood glucose level sent by a wireless blood glucose meter (a type of biological sample measurement apparatus), the portable terminal transmits the acknowledge signal to the wireless blood glucose meter. The wireless blood glucose meter stores as a piece of history information the transmission power when the blood glucose level was sent and whether or not the acknowledge signal was received for that transmission, and determines the transmission power during transmission on the basis of this history information.

In the past, the optimization of transmission power in a wireless terminal device was performed on the basis of the error rate during transmission and reception. With this method, though, the transmission power cannot be optimized unless a specific volume of data is transmitted or received, so the transmission power cannot be optimized if an extremely small quantity of data is sent wirelessly, such as a blood glucose level measured with a wireless blood glucose meter, for example.

In view of this, with the biological sample measurement apparatus of the present invention, the transmission power when the transmitter transmits biological data and whether or not an acknowledge signal has been received for that transmission are stored as history information, and the transmission power during transmission by the transmitter is determined on the basis of this history information. Also, the transmission power may be determined on the basis of history information extracted according to a transmission power determination rule that sets forth the specific extraction conditions.

Consequently, it is possible, for example, to determine, as the transmission power of the transmitter, transmission power in a piece of history information indicating that the biological data sent by the transmitter has been properly received. For example, even though a specific volume of data has not been sent or received between the wireless blood glucose meter and the portable terminal, it is possible to determine as the transmission power of the transmitter transmission power in a piece of history information for which the acknowledge signal has been received, that is, a piece of history information at which intercommunication was possible between the wireless blood glucose meter and the portable terminal. Also, for example, if there are a plurality of pieces of history information at which intercommunication was possible between the wireless blood glucose meter and the portable terminal, the lowest transmission power in the plurality of pieces of history information can be determined as the transmission power of the transmitter.

As a result, optimization of the transmission power can be achieved regardless of the volume of data being sent.

The biological sample measurement apparatus pertaining to the second invention is the biological sample measurement apparatus pertaining to the first invention, wherein the transmission power determiner extracts a specific number of pieces of the history information according to the transmission power determination rule, and determines the transmission power of the transmitter so that the transmission power of the transmitter is lower than the transmission power stored as the history information, when the extracted history information includes at least a specific number of pieces of the history information for which the acknowledge signal has been received.

Here, if there are at least a specific number of pieces of the history information for which the acknowledge signal has been received, that is, the history information indicating that the biological data sent by the transmitter has been properly received, the transmission power determiner decides that the output of the transmission power is sufficient in transmission by the transmitter, and the transmission power is lowered by a specific value.

The transmission power determination rule referred to here means the conditions for extracting the history information, such as a condition that the extraction will be performed in the order of newest to oldest, or a condition that the extraction will be performed on the same day of the week or at the same time of day as when the biological data is measured.

Here, the transmission power in transmission by the transmitter is preferably kept as low as possible, while still allowing communication, in order to reduce power consumption.

Consequently, the transmission power of the transmitter can be lowered while still allowing communication, so a power saving can be obtained.

The biological sample measurement apparatus pertaining to the third invention is the biological sample measurement apparatus pertaining to the first invention, wherein the transmission power determiner extracts a specific number of pieces of the history information according to a transmission power determination rule, and determines the transmission power of the transmitter so that the transmission power of the transmitter is higher than the transmission power stored as the history information, when the extracted history information does not include at least a specific number of pieces of the history information for which the acknowledge signal has been received.

Here, if there are not at least a specific number of pieces of the history information indicating that the biological data sent by the transmitter has been properly received, the transmission power determiner decides that the output of the transmission power is insufficient in transmission by the transmitter, and the transmission power is raised by a specific value.

Consequently, the transmission power can be determined more optimally so that the biological data sent by the transmitter can be received properly. For instance, in the relationship between a wireless blood glucose meter and a portable terminal, the transmission power can be determined more optimally so that the data sent from the wireless blood glucose meter can be properly received by the portable terminal.

The biological sample measurement apparatus pertaining to the fourth invention is the biological sample measurement apparatus pertaining to any of the first to third inventions, further comprising a noise power measurement component for measuring noise power just before the transmitter transmits, wherein the storage component further stores as the history information the noise power measured by the noise power measurement component.

Here, a noise power measurement component that measures the noise power just before transmission by the transmitter is further provided in order to take into account the noise power in determining the transmission power in transmission by the transmitter. The storage component stores the noise power measured by the noise power measurement component as history information along with whether or not there is an acknowledge signal and the transmission power when the transmitter transmits biological data.

Here, noise power generally has an adverse effect on communication between wireless terminal devices.

Consequently, the effect of noise power can be taken into account in determining transmission power.

The biological sample measurement apparatus pertaining to the fifth invention is the biological sample measurement apparatus pertaining to the fourth invention, wherein the transmission power determiner extracts the history information for which the acknowledge signal has been received according to the transmission power determination rule, and determines the transmission power of the transmitter on the basis of the noise power measured by the noise power measurement component, so that a ratio of the measured noise power to the transmission power of the transmitter is the same as a ratio of the noise power to the transmission power in the extracted history information.

Here, the ratio of noise power to transmission power, which is the inverse of so-called S/N ratio, is calculated from the history information indicating that the biological data sent by the transmitter has been properly received. Since the noise power during transmission is a known condition by noise power measurement component, the transmission power during transmission by the transmitter is determined so as to obtain the inverse of the above-mentioned S/N ratio on the basis of this.

Consequently, the effect of noise power on communication can be taken into account, so the transmission power can be determined more optimally.

The biological sample measurement apparatus pertaining to the sixth invention is the biological sample measurement apparatus pertaining to the fourth invention, wherein the transmission power determiner extracts a specific number of pieces of the history information according to the transmission power determination rule, and determines the transmission power of the transmitter on the basis of the noise power measured by the noise power measurement component, so that a ratio of the measured noise power to the transmission power of the transmitter is greater than the ratio of the noise power to the transmission power in the history information, when the extracted history information includes at least a specific number of pieces of the history information for which the acknowledge signal has been received.

Here, if there are at least a specific number of pieces of history information indicating that the biological data sent by the transmitter has been properly received, the transmission power determiner determines that the transmission power is sufficient in transmission by the transmitter, and the S/N ratio is lowered by a specific value.

Here, the transmission power in transmission by the transmitter is preferably kept as low as possible, while still allowing communication, in order to reduce power consumption.

Consequently, the transmission power of the transmitter can be lowered while still allowing communication, so a power saving can be obtained.

The biological sample measurement apparatus pertaining to the seventh invention is the biological sample measurement apparatus pertaining to the fourth invention, wherein the transmission power determiner extracts a specific number of pieces of the history information according to a transmission power determination rule, and determines the transmission power of the transmitter with respect to the noise power measured by the noise power measurement component, so that a ratio of the measured noise power to the transmission power of the transmitter is less than the ratio of the noise power to the transmission power in the history information, when the extracted history information does not include at least a specific number of pieces of the history information for which the acknowledge signal has been received.

Here, if there are at least a specific number of pieces of history information indicating that the biological data sent by the transmitter has been properly received, the transmission power determiner determines that the transmission power is insufficient in transmission by the transmitter, and the S/N ratio is raised by a specific value.

Consequently, the transmission power can be determined more optimally so that the biological data sent by the transmitter can be properly received. For instance, in the relationship between a wireless blood glucose meter and a portable terminal, the transmission power can be determined more optimally so that the data sent from the wireless blood glucose meter can be properly received by the portable terminal.

The biological sample measurement apparatus pertaining to the eighth invention is a biological sample measurement apparatus for communicating wirelessly with an external device, comprising a biological data measurement component, a transmitter, a receiver, a storage component, and a transmission power determiner. The biological data measurement component measures the biological data. The transmitter transmits the biological data measured by the biological data measurement component. The receiver receives an acknowledge signal that is returned when the external device has properly received the biological data transmitted by the transmitter. The storage component stores a reference reception power that is the optimal reception power when the external device receives the biological data, and the history information that includes whether or not an acknowledge signal was received and transmission power when the transmitter transmitted the biological data, and reception power when the external device has received the biological data. The transmission power determiner determines transmission power when the transmitter transmits on the basis of the history information and the reference reception power stored in the storage component, or the history information extracted according to a transmission power determination rule that sets forth extraction conditions and the reference reception power.

Here, whether or not an acknowledge signal was received and the transmission power when the transmitter transmitted biological data, and the reception power when an external device received the biological data, are stored in the storage component as history information, or the optimal reception power when the external device receives the biological data is stored as a reference reception power. The transmission power determiner determines the transmission power in transmission by the transmitter on the basis of the history information and reference reception power stored in the storage component, or the history information extracted according to a transmission power determination rule that sets forth extraction conditions and the reference reception power.

The "reception power when an external device received the biological data" here can be stored in the storage component by replying simultaneously with the acknowledge signal returned by the external device, and receiving the acknowledge signal. The "reference reception power" defines the reception power for an external device to properly receive biological data, that is, the optimal reception power in receiving biological data. If we ignore the external environment and so forth, an external device can generally receive biological data properly if the transmitter sends at transmission power corresponding to the reference reception power.

In the past, the optimization of transmission power in a wireless terminal device was performed on the basis of the error rate during transmission and reception. With this method, though, the transmission power cannot be optimized unless a specific volume of data is transmitted or received, so the transmission power cannot be optimized if an extremely small quantity of data is sent wirelessly, such as a blood glucose level measured with a wireless blood glucose meter, for example.

In view of this, with the biological sample measurement apparatus of the present invention, a reference reception power that is the optimal reception power for the external device, and history information including the transmission power when the transmitter transmitted biological data, whether or not an acknowledge signal was received for this transmission, and the reception power when an external device received the biological data are stored, and the transmission power in transmission by the transmitter is determined on the basis of this history information and reference reception power. Also, the transmission power may be determined on the basis of the history information extracted according to a transmission power determination rule that sets forth specific extraction conditions, and reference reception power.

Consequently, the transmission power in transmission by the transmitter can be determined by comparing the reference reception power stored in the storage component with, for example, the most recent history information for which an acknowledge signal has been received. Accordingly, for example, even though a specific volume of data has not been sent or received between the wireless blood glucose meter and the portable terminal, it is possible to determine the transmission power in transmission by the transmitter on the basis of the history information stored in the storage component.

As a result, optimization of the transmission power can be achieved regardless of the volume of data being sent.

The biological sample measurement apparatus pertaining to the ninth invention is the biological sample measurement apparatus pertaining to the eighth invention, wherein the transmission power determiner extracts one piece of the history information according to the transmission power determination rule, and compares the reception power in the extracted history information with the reference reception power, and if the reception power is higher than the reference reception power, the transmission power when the transmitter transmits is determined so as to be lower than the transmission power stored as the extracted history information, and if the reception power is lower than the reference reception power, the transmission power when the transmitter transmits is determined so as to be higher than the transmission power stored as the extracted history information.

Here, of the history information for which an acknowledge signal has been received, that is, the history information indicating that the biological data sent by the transmitter has been properly received, the most recent history information is extracted, for example. The reference reception power and the reception power included in the extracted history information are compared, and the transmission power in transmission by the transmitter is determined on the basis of the comparison result.

The transmission power at which the transmitter transmits and the reception power at which the external device receives may differ with the external environment and so forth. The external environment here also encompasses the remaining battery charge of the external device, and situations such as when the external device has been replaced.

Consequently, the transmission power in transmission by the transmitter can be determined on the basis of the reception power when the external device on the reception side actually received biological data. As a result, the transmission power can be properly optimized even when the transmission power in transmission by the transmitter and the reception power when received by the external device are different due to the external environment or the like.

The biological sample measurement apparatus pertaining to the tenth invention is the biological sample measurement apparatus pertaining to the eighth or ninth invention, wherein the transmission power determiner extracts a specific number of pieces of the history information according to the transmission power determination rule, and if the extracted history information includes at least a specific number of pieces of the history information for which the acknowledge signal has been received, the reference reception power is set lower than the value stored in the storage component.

Here, if there are at least a specific number of pieces of history information for which an acknowledge signal has been received, that is, history information indicating that the biological data sent by the transmitter has been properly received, the transmission power determiner decides that the output of reception power is sufficient in reception by an external device, and lowers the reference reception power by a specific value.

The transmission power determination rule referred to here means the conditions for extracting history information, such as a condition that the extraction will be performed in the order of newest to oldest, or a condition that the extraction will be performed on the same day of the week or at the same time of day as when the biological data is measured.

Here, the transmission power in transmission by the transmitter is preferably kept as low as possible, while still allowing communication, in order to reduce power consumption. That is, since the transmission power in transmission by the transmitter is determined on the basis of the reference reception power, the transmission power in transmission by the transmitter can be lowered by lowering the reference reception power.

Consequently, the transmission power in transmission by the transmitter can be lowered while still allowing communication, so a power saving can be obtained.

The biological sample measurement apparatus pertaining to the eleventh invention is the biological sample measurement apparatus pertaining to the eighth or ninth invention, wherein the transmission power determiner extracts a specific number of pieces of the history information according to the transmission power determination rule, and if the extracted history information does not include at least a specific number of pieces of the history information for which the acknowledge signal has been received, the reference reception power is set higher than the value stored in the storage component.

Here, if there are not at least a specific number of pieces of history information indicating that the biological data sent by the transmitter has been properly received, the transmission power determiner decides that the output of reception power is insufficient in reception by an external device, and raises the reference reception power by a specific value.

Here, since the transmission power in transmission by the transmitter is determined on the basis of the reference reception power, the transmission power in transmission by the transmitter can be raised by raising the reference reception power.

Consequently, the transmission power can be optimally determined so that the biological data sent by the transmitter can be properly received. For instance, in the relationship between a wireless blood glucose meter and a portable terminal, the reference reception power can be set optimally so that the data sent from the wireless blood glucose meter can be properly received by the portable terminal.

The biological sample measurement apparatus pertaining to the twelfth invention is the biological sample measurement apparatus pertaining to any of the first to eleventh inventions, wherein the transmission power determination rule is set up so as to extract the history information in the order of newest to oldest.

Here, the transmission power determination rule is set up so that the history information stored in the storage component is extracted in the order of newest to oldest.

Consequently, this will reflect the latest information, which is generally more reliable, so the transmission power can be determined more optimally.

The biological sample measurement apparatus pertaining to the thirteenth invention is the biological sample measurement apparatus pertaining to any of the first to twelfth inventions, wherein the transmission power determination rule is set up so as to extract, from among the history information stored in the storage component, the history information for the same day of the week as when the history information is extracted by the transmission power determiner.

Here, the optimal transmission power to be transmitted by the transmitter will vary with the environment in which the biological sample measurement apparatus is used. It is considered most likely that on a given day of the week, the user will generally use the biological sample measurement apparatus in the same place, that is, in the same environment. Accordingly, it is considered most likely that history information for which there is an acknowledge signal corresponding to the same conditions (same day of the week) as when the history information is extracted, that is, when a measurement is made with the biological sample measurement apparatus, will afford the optimal transmission power.

Consequently, the environment in which the biological sample measurement apparatus is used can be taken into account, so the transmission power can be determined more optimally.

The biological sample measurement apparatus pertaining to the fourteenth invention is the biological sample measurement apparatus pertaining to any of the first to thirteenth inventions, wherein the transmission power determination rule is set up so as to extract the history information of the same time period as when the history information is extracted by the transmission power determiner.

Here, the transmission power determination rule is set up so that, of the history information stored in the storage component, the history information of the same time period as when the history information was extracted by the transmission power determiner will be extracted.

As mentioned above, in a given time period, it is considered most likely that the user will generally use the biological sample measurement apparatus in the same place, that is, in the same environment. Also, this is considered even more likely if both the day of the week and the time of day are the same. Accordingly, it is considered most likely that history information for which there is an acknowledge signal corresponding to the same conditions (same time of day) as when the history information was extracted, that is, when a measurement was made with the biological sample measurement apparatus, will afford the optimal transmission power.

Consequently, the environment in which the biological sample measurement apparatus is used can be taken into account, so the transmission power can be determined more optimally.

The biological sample measurement apparatus pertaining to the fifteenth invention is the biological sample measurement apparatus pertaining to any of the first to fourteenth inventions, wherein the transmission power determiner determines the maximum transmission power which the transmitter is able to output if the biological data measured by the biological data measurement component is not a value within a specific range.

Here, if the biological data measured by the biological data measurement component is higher than a specific value, the biological data is sent at the maximum transmission power at which the transmitter is able to output. For example, when a diabetes patient is using a wireless blood glucose meter, if the blood glucose level measured by the wireless blood glucose meter is higher than a specific value, the blood glucose level is sent at the maximum transmission power at which the transmitter is able to output to the portable terminal.

Consequently, it is possible to lower the probability that the biological data sent by the transmitter cannot be received due to some kind of problem. For instance, if the blood glucose level measured by a wireless blood glucose meter is higher than a specific value, that is, if there is an urgent need for treatment by a physician or the like, it is possible to lower the probability of a situation in which the portable terminal cannot receive the blood glucose level.

The biological sample measurement apparatus pertaining to the sixteenth invention is the biological sample measurement apparatus pertaining to any of the first to fifteenth inventions, further comprising an interface having a display component for displaying the biological data measured by the biological data measurement component, an operating setting component for allowing the user to make various operating settings, and an alarm sound output component for outputting an alarm sound, wherein, if the biological data measured by the biological data measurement component is lower than a specific value, an alarm sound is outputted from the alarm sound output component, and an emergency status is displayed on the display component.

Here, if the biological data measured by the biological data measurement component is lower than a specific value, the alarm sound output component outputs an alarm sound, and some kind of message is displayed on the display component.

A blood glucose level that is below a specific value represents a dangerous situation to a diabetes patient, and in some cases can lead to impaired consciousness.

In view of this, when a diabetes patient uses a wireless blood glucose meter to measure a blood glucose level, for example, if that value is lower than a specific value, the alarm sound output component outputs an alarm sound, and how to deal with hypoglycemia or another such message is displayed on the display component.

Consequently, the user himself or a person close to the user of the biological sample measurement apparatus can be alerted that the user is in a dangerous situation. Also, even if the person using the wireless blood glucose meter should lose consciousness, a person nearby will be able to take the appropriate measures by looking at the message displayed on the display component.

The biological sample measurement apparatus pertaining to the seventeenth invention is the biological sample measurement apparatus pertaining to the sixteenth invention, wherein the emergency status is a telephone number.

Here, if the user is in an extremely dangerous situation, a telephone number is displayed on the display component.

Consequently, for example, even if the person using the wireless blood glucose meter should lose consciousness, someone nearby can look at the telephone number displayed on the display component and immediately contact a family member of the patient or a personal physician, and so on.

The biological sample measurement apparatus pertaining to the eighteenth invention is the biological sample measurement apparatus pertaining to the sixteenth or seventeenth invention, wherein the emergency status is a method for treating hypoglycemia.

Here, if the user is in an extremely dangerous situation, how to deal with the situation is displayed on the display component.

Consequently, for example, even if the person using the wireless blood glucose meter should lose consciousness, someone nearby can look at the message displayed on the display component and take the appropriate measures.

The biological sample measurement apparatus pertaining to the nineteenth invention is the biological sample measurement apparatus pertaining to any of the first to eighteenth inventions, wherein the biological data measurement component is a wireless blood glucose meter constituted so as to measure a blood glucose level.

Consequently, for example, even if a specific volume of data is not sent or received between a wireless blood glucose meter and a portable terminal, the transmission power in the history information stored in the storage component with which an acknowledge signal has been received, that is, with which communication is possible between the wireless blood glucose meter and the portable terminal, can be determined as the transmission power in transmission by the transmitter.

As a result, transmission power can be optimized regardless of the volume of data being transmitted.

The biological sample measurement system pertaining to the twentieth invention comprises a biological sample measurement apparatus and an external device. The biological sample measurement apparatus is the biological sample measurement apparatus pertaining to any of the eighth to eleventh inventions. The external device has an external receiver, an error detector, an external transmitter, a reception power determiner, and a transmission power selector. The external receiver receives biological data transmitted from the biological sample measurement apparatus. The error detector determines whether or not the external receiver has properly received the biological data. The external transmitter transmits an acknowledge signal to the biological sample measurement apparatus when the error detector has determined that the biological data has been properly received. The reception power determiner measures the reception power when the external receiver has received the biological data, and compares this with a specific value. The transmission power selector selects the transmission power of the external transmitter on the basis of the determination result of the reception power determiner.

Consequently, it is possible for an acknowledge signal to be received properly with a biological sample measurement apparatus.

The biological sample measurement system pertaining to the twenty-first invention is the biological sample measurement system pertaining to the twentieth invention, wherein the transmission power selector selects the maximum power as the transmission power in the external transmitter when the reception power determiner has determined that the reception power when the biological data has been received by the external receiver is lower than the specific value.

Consequently, there will be no situations in which an acknowledge signal cannot be received in a biological sample measurement apparatus even though data was properly sent from the biological sample measurement apparatus to an external device.

Advantageous Effects

The biological sample measurement apparatus pertaining to the present invention, and the biological sample measurement system equipped with this apparatus, make it possible to optimize the transmission power regardless of the volume of data being sent.

BRIEF DESCRIPTION OF DRAWINGS

FIG. 8 is a diagram illustrating the storage format in the first embodiment of the present invention;

FIG. 15 is a diagram illustrating the storage format in the second embodiment of the present invention;

FIG. 18 is a diagram illustrating the storage format in a third embodiment of the present invention;

Figure 1:
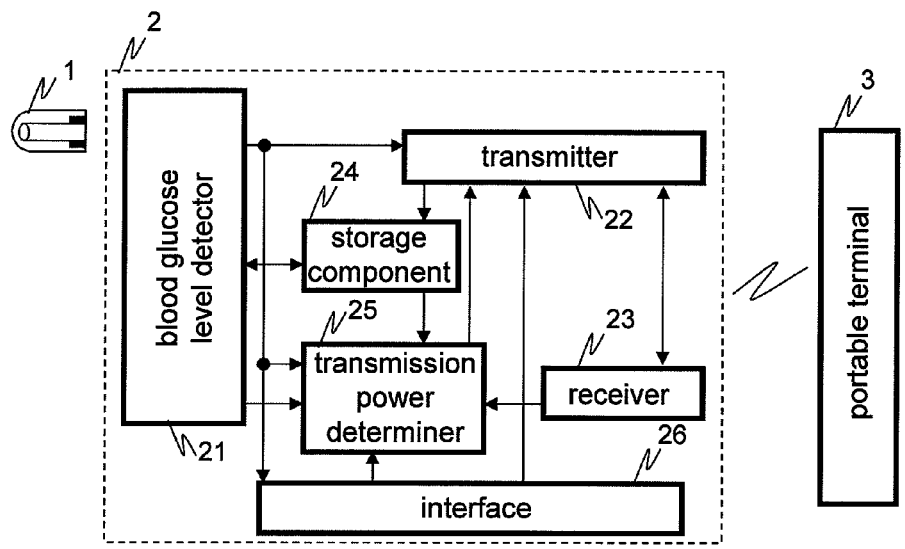
FIG. 1 is a block diagram of a wireless blood glucose meter and a peripheral device in a first embodiment of the present invention.

EXPLANATION OF REFERENCE 1 biosensor
2 wireless blood glucose meter (biological sample measurement apparatus)
3 portable terminal (external device)
4 blood glucose level measurement system (biological sample measurement system)
11 working electrode
12 counter electrode
13 reactant
21 blood glucose level detector (biological data measurement component)
22 transmitter
23 receiver
24 storage component
25 transmission power determiner
26 interface
28 noise power acquisition component (noise power measurement component)
211 connector
212 computation amplifier
213 feedback resistor
214 reference potential
215 A/D conversion circuit
216 computation circuit
221 transmission control circuit
222 optimal power holding register
223 maximum power holding register
224 selector
225 transmission circuit
231 reception control circuit
232 reception circuit
233 preamble detection circuit
234 sync pattern detection circuit
235 demodulation circuit
236 reception register
237 error detection circuit
241 memory
242 memory control circuit
243 arbitration circuit
244 condition identification circuit
245 current pointer
246 address generation circuit
247 data register
251 transmission power control circuit
252 conversion table
253 transmission power selector
254 transmission power register
255 transmission power control circuit
256 noise power register
261 operating setting component
262 display component
263 alarm sound output component
264 time manager
A1 receiver (external receiver)
A2 reception power determiner
A3 error detector
A4 storage component A5 transmission power selector
A6 transmitter (external transmitter)

BEST MODE FOR CARRYING OUT THE INVENTION

First Embodiment

A wireless blood glucose meter (biological sample measurement apparatus) 2 pertaining to an embodiment of the present invention will now be described through reference to FIGS. 1 to 12.

Constitution of Wireless Blood Glucose Meter 2

A blood glucose level (biological data) is measured about eight times a day with the wireless blood glucose meter 2. The user of the wireless blood glucose meter 2 connects an electrochemical, disposable biosensor 1 to the wireless blood glucose meter 2, and puts a spot of blood on the biosensor 1.

The wireless blood glucose meter 2 detects the blood glucose level from the connected biosensor 1, and sends the detected blood glucose level data to a portable terminal (external device) 3 used to load measurement data about a patient by a physician or the like. The portable terminal 3 sends an acknowledge signal to the wireless blood glucose meter 2 upon receiving the blood glucose level data from the wireless blood glucose meter 2.

Explanation of Internal Operation of Wireless Blood Glucose Meter 2

The internal operation of the wireless blood glucose meter 2 will now be described through reference to the block diagram of FIG. 1, which illustrates a wireless blood glucose meter and a peripheral device in an embodiment of the present invention.

As shown in FIG. 1, the wireless blood glucose meter 2 has a blood glucose level detector (biological data measurement component) 21, a transmitter 22, a receiver 23, a storage component 24, a transmission power determiner 25, and an interface 26.

The blood glucose level detector 21 measures a blood glucose level from a spot of blood placed on the biosensor 1. The blood glucose level thus measured is then transferred to the transmitter 22, the transmission power determiner 25, and the interface 26.

The transmission power determiner 25 determines the transmission power from the history information stored in the storage component 24, and from the blood glucose level outputted from the blood glucose level detector 21.

The transmitter 22 sends the blood glucose level data detected by the blood glucose level detector 21 at the transmission power determined by the transmission power determiner 25.

Here, the portable terminal 3 sends an acknowledge signal upon receiving blood glucose level data sent from the transmitter 22.

Upon receiving an acknowledge signal from the portable terminal 3, the receiver 23 outputs to the transmitter 22 information indicating that an acknowledge signal has been received.

If the receiver 23 has received an acknowledge signal, information indicating that an acknowledge signal has been received from the portable terminal 3 and the transmission power in transmission by the transmitter 22 are stored as history information in the storage component 24. Also, if an acknowledge signal cannot be received by the receiver 23 within 600 ms even though the transmitter 22 has sent a blood glucose level to the portable terminal 3, information indicating that an acknowledge signal has been received and the transmission power in transmission by the transmitter 22 are stored as history information. If the receiver 23 cannot receive an acknowledge signal, the transmitter 22 sets the transmission power to the maximum value possible and resends the blood glucose level data to the portable terminal 3. This retransmission of the blood glucose level data is performed five times at most, until the receiver 23 receives an acknowledge signal, but acknowledge signal receipt information with respect to the retransmission and the transmission power of the transmitter 22 are not stored in the storage component 24.

The interface 26 serves as an interface component when the user operates the wireless blood glucose meter 2, and has an operating setting component 261 and a display component 262, for example. The interface 26 will be discussed in detail later.

Because the wireless blood glucose meter 2 is constituted as above, even if a specific volume of data is not sent or received between the wireless blood glucose meter 2 and the portable terminal 3, the transmission power in history information indicating acknowledge signal receipt stored in the storage component 24 can be determined as the transmission power during transmission by the transmitter 22. As a result, the transmission power can be optimized regardless of the volume of data being sent.

Explanation of Internal Blocks of Wireless Blood Glucose Meter 2

The internal blocks of the wireless blood glucose meter 2 will now be described in detail.

Blood Glucose Level Detector 21

The blood glucose level detector 21 will be described in detail through reference to FIG. 2, which is a block diagram of the blood glucose level detector 21.

Figure 2:
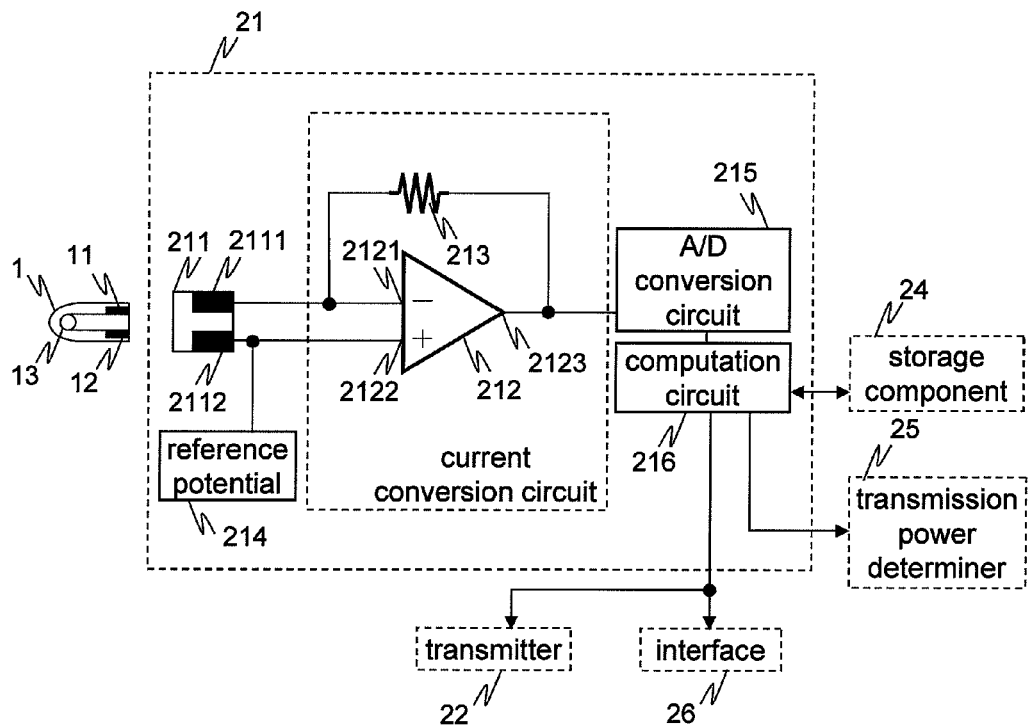
FIG. 2 is a block diagram of a blood glucose level detector in the first embodiment of the present invention.

As shown in FIG. 2, the blood glucose level detector 21 has a connector 211, a computation amplifier 212, a feedback resistor 213, an A/D conversion circuit 215, and a computation circuit 216.

The biosensor 1 here is a disposable, electrochemical type, and has a working electrode 11, a counter electrode 12, and a reactant 13. The working electrode 11 comes into contact with an electrode 2111 when the biosensor 1 is inserted into the connector 211. The counter electrode 12 comes into contact with an electrode 2112 when the biosensor 1 is inserted into the connector 211. The reactant 13 is formed from an enzyme, a mediator, or the like. When a spot of blood is placed on the reactant 13, the reactant 13 dissolves in the blood and undergoes an enzyme reaction.

The connector 211 is an insertion opening for inserting the biosensor 1, and has the electrode 2111 and the electrode 2112. When the biosensor 1 is inserted into the connector 211, the electrode 2111 comes into contact with the working electrode 11 included in the biosensor 1, and the electrode 2112 comes into contact with the counter electrode 12 included in the biosensor 1.

The computation amplifier 212 applies voltage to the working electrode 11 and the counter electrode 12 through the electrode 2111 in contact with the working electrode 11 of the biosensor 1 and the electrode 2112 in contact with the counter electrode 12 of the biosensor 1. Current that is correlated to the glucose concentration in the blood flows through the feedback resistor 213 to the biosensor 1 at this point. A non-inverting input terminal 2122 of the computation amplifier 212 is connected to a reference potential 214 here. The computation amplifier 212 controls so as to keep the non-inverting input terminal 2122 and an inverting input terminal 2121 at the same potential, so a voltage in which the reference potential 214 is added to the potential drop produced by the current of the feedback resistor 213 is generated at an output terminal 2123. Consequently, a voltage that is proportional to the current flowing to the biosensor 1 is generated at the output terminal 2123, and current-voltage conversion can be performed.

The A/D conversion circuit 215 converts the voltage generated at the output terminal 2123 into a digital value. The A/D conversion circuit 215 sends the converted digital value to the computation circuit 216.

The computation circuit 216 computes the digital value sent from the A/D conversion circuit. Consequently, the glucose concentration in the blood can be calculated from the value for the current flowing to the biosensor 1. The computation circuit 216 transfers the calculated glucose concentration to the transmitter 22 and the interface 26.

The following processing, for example is carried out in obtaining the glucose concentration in the blood.

Ahead of time, at the factory, two constant current supplies that generate current equivalent to a low glucose concentration and a high glucose concentration are connected between the electrode 2111 and the electrode 2112 of the connector 211, and a linear conversion expression for the current value and the digital value is found with the computation circuit 216 from the A/D conversion values of each. The slope a and the intercept b of this linear expression are information that correlates the glucose concentration and the digital value outputted from the A/D conversion circuit 215, and this information is stored in the storage component 24. Then, when the user measures a blood glucose level, the computation circuit 216 calculates the glucose concentration in the blood by plugging the digital value obtained from the A/D conversion circuit 215 into the linear expression stored in the storage component 24. The calculated blood glucose level is transferred to the transmitter 22, the transmission power determiner 25, and the interface 26. An actuation pulse for calculating the transmission power is also produced for the transmission power determiner 25.

Transmitter 22

The transmitter 22 will now be described in detail through reference to FIG. 3, which is a block diagram of the transmitter 22, and FIG. 4, which is a control flowchart for the transmitter 22.

Figure 3:
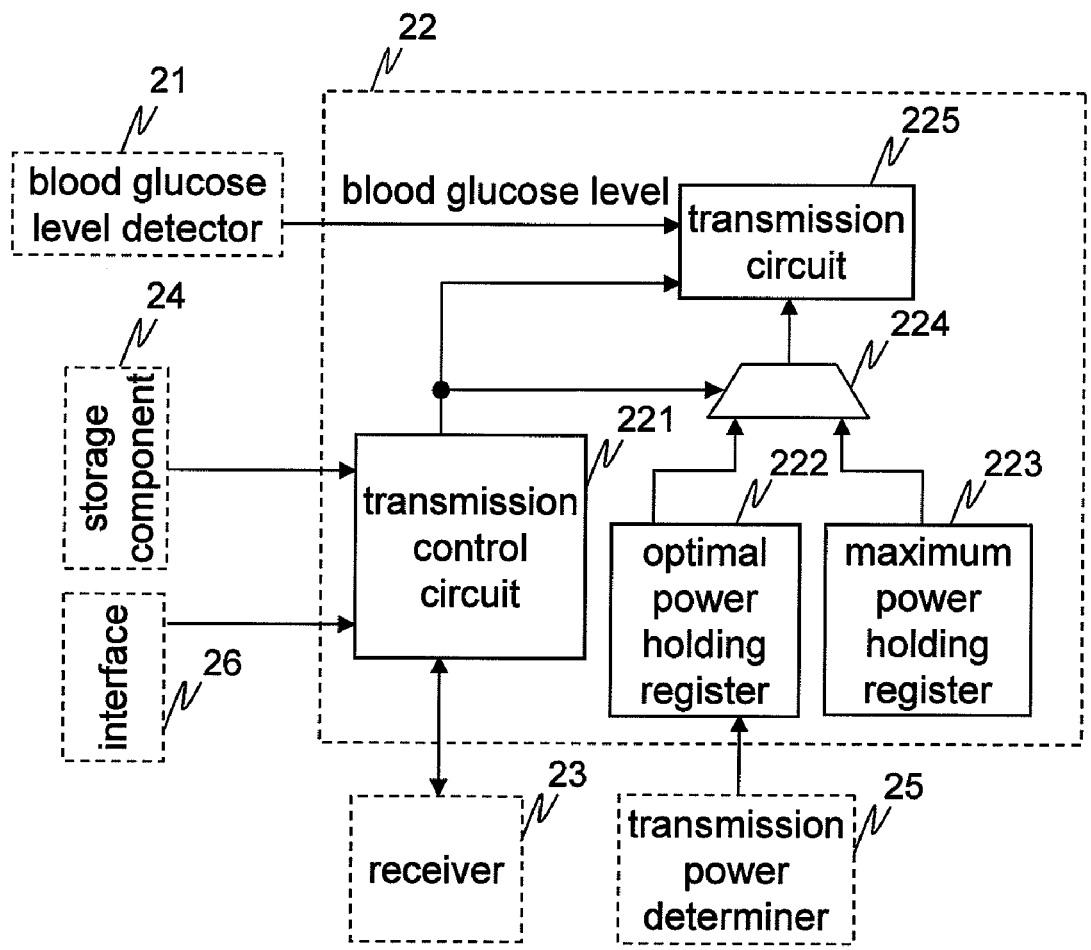
FIG. 3 is a block diagram of a transmitter in the first embodiment of the present invention.
Figure 4:
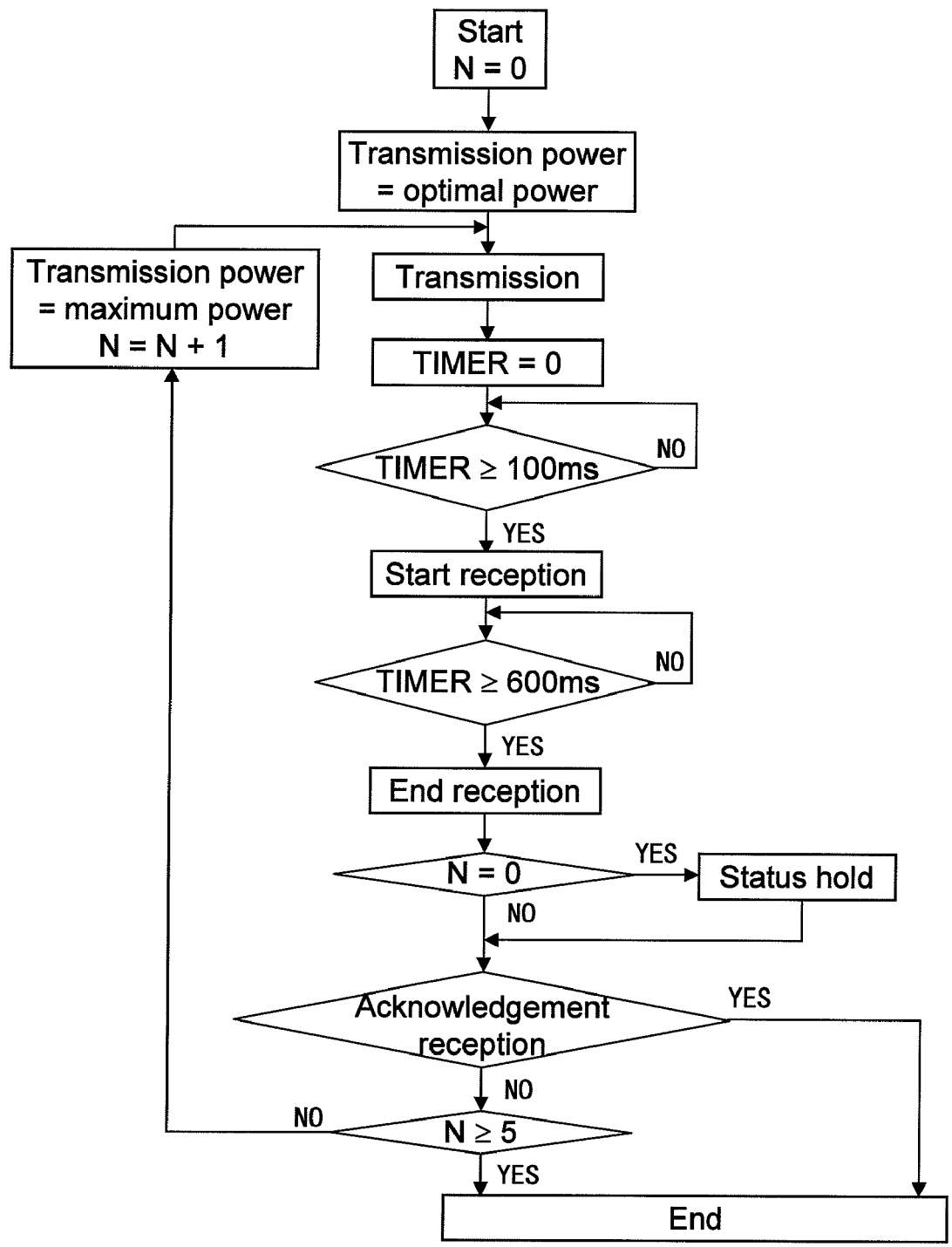
FIG. 4 is a control flowchart of the transmitter in the first embodiment of the present invention.

As shown in FIG. 3, the transmitter 22 has a transmission control circuit 221, an optimal power holding register 222, a maximum power holding register 223, and a transmission circuit 225.

The transmission control circuit 221 controls the selector 224 and the transmission circuit 225.

The optimal power holding register 222 holds the optimal power outputted from the transmission power determiner 25.

The maximum power holding register 223 holds the maximum transmission power that can be sent by the wireless blood glucose meter 2.

The selector 224 switches the power outputted to the transmission circuit 225 between the optimal power holding register 222 and the maximum power holding register 223.

The transmission circuit 225 takes the blood glucose level data sent from the blood glucose level detector 21 and sends it to the portable terminal 3 at the power sent from the selector 224.

The transmission control circuit 221 switches the selector 224 so that when the optimal power is written to the optimal power holding register 222, the optimal power stored in the optimal power holding register 222 is outputted to the transmission circuit 225. The transmission control circuit 221 also instructs the transmission circuit 225 to send the blood glucose level outputted from the blood glucose level detector 21 to the portable terminal 3. Consequently, the transmission circuit 225 can send the blood glucose level outputted from the blood glucose level detector 21 to the portable terminal 3 at the optimal power. The transmission circuit 225 creates transmission data by modulating the product of adding an error detection code to the measurement data, then adds a preamble pattern and a sync pattern to the head of this, and sends this to the portable terminal 3. The transmission control circuit 221 issues a command to transmit to the transmission circuit 225, and begins counting with an internal timer. The portable terminal 3 sends out an acknowledge signal 500 ms after the receipt of the blood glucose level data. The transmission control circuit 221 instructs the receiver 23 to begin receiving 100 ms after transmission, and ends the receipt by the receiver 23 600 ms after the start of transmission.

Next, the transmission control circuit 221 confirms whether or not an acknowledge signal has been received by the receiver 23. If the receiver 23 has received an acknowledge signal from the portable terminal 3, the transmission control circuit 221 controls the transmission circuit 225 so that the transmission of the blood glucose level to the portable terminal 3 is ended. At this point, the transmission control circuit 221 uses the day of the week and time information inputted from the interface 26 and stores "the day of transmission, the transmission start time, the transmission power during transmission, and whether or not an acknowledge signal has been received" as history information in the storage component 24.

Meanwhile, if the receiver 23 has not received an acknowledge signal from the portable terminal 3, the transmission control circuit 221 switches the selector 224 so that the value stored in the maximum power holding register 223 is inputted to the transmission circuit 225. The transmission control circuit 221 then instructs the transmission circuit 225 to resend the blood glucose level. Consequently, the transmission circuit 225 can send the blood glucose level outputted from the blood glucose level detector 21 to the portable terminal 3 at the maximum transmission power at which the wireless blood glucose meter 2 is able to transmit.

The retransmission of the blood glucose level by the transmission circuit 225 is performed in a similar way with the first transmission, up to a maximum of five times. However, the various information mentioned above is not stored as history information in the storage component 24.

If, after the blood glucose level has been retransmitted five times by the transmission circuit 225, an acknowledge signal has not been received even once from the portable terminal 3, the transmission control circuit 221 instructs the transmission circuit 225 to end the transmission of the blood glucose level.

Receiver 23

Next, the receiver 23 will be described in detail through reference to FIG. 5, which is a block diagram of the receiver 23, and FIG. 6, which is a control flowchart for the receiver 23.

Figure 5:
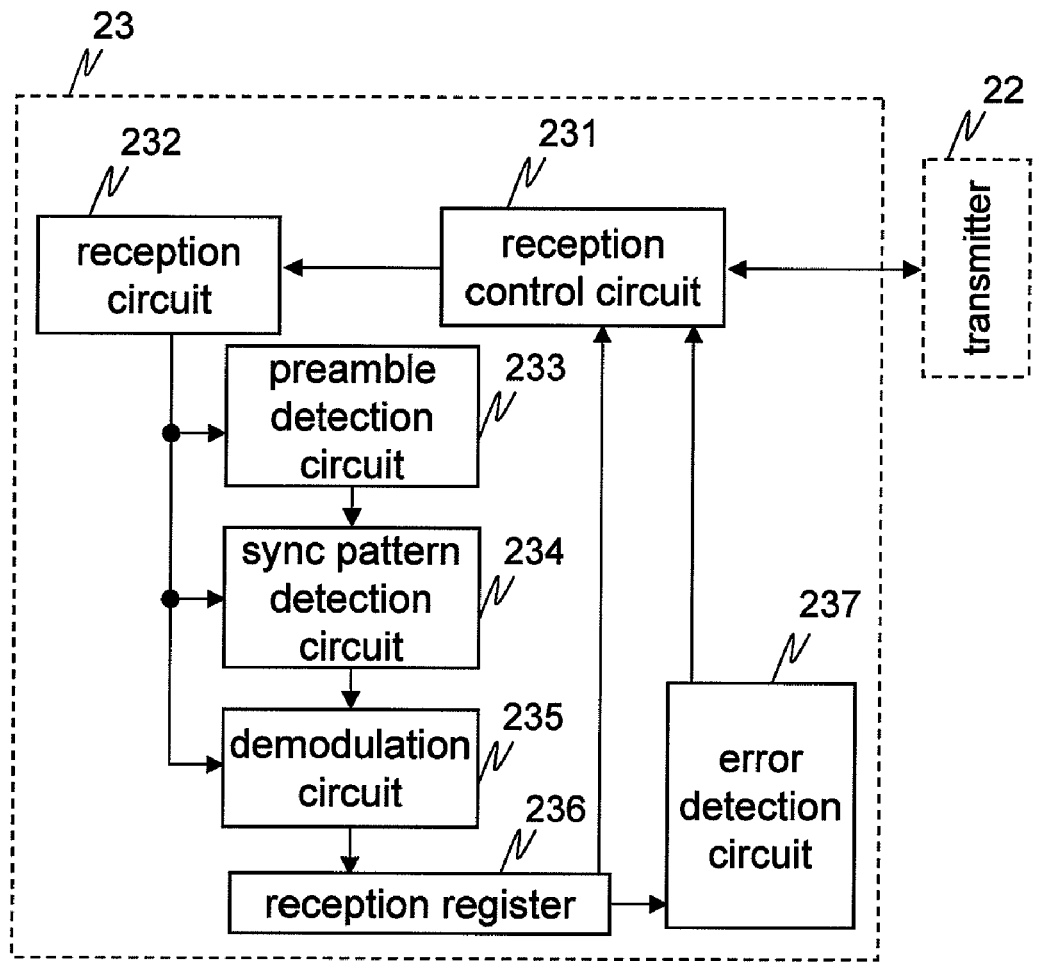
FIG. 5 is a block diagram of a receiver in the first embodiment of the present invention.

As shown in FIG. 5, the receiver 23 has a reception control circuit 231, a reception circuit 232, a preamble detection circuit 233, a sync pattern detection circuit 234, a demodulation circuit 235, a reception register 236, and an error detection circuit 237.

The reception control circuit 231 receives a reception commencement command from the transmitter 22, and controls the reception circuit 232.

The reception circuit 232 performs detection of carrier waves from received signals, gain control, conversion to intermediate frequencies, and other such processing, and transfers the processed data to the preamble detection circuit 233, the sync pattern detection circuit 234, and the demodulation circuit 235.

The preamble detection circuit 233 performs detection of a preamble pattern. When a preamble pattern is detected, the preamble detection circuit 233 outputs an actuation pulse to the sync pattern detection circuit 234.

The sync pattern detection circuit 234 performs detection of a sync pattern from reception data outputted from the reception circuit 232, by means of the actuation pulse from the preamble detection circuit 233.

The demodulation circuit 235 performs demodulation of reception data using as a reference the sync pattern detected by the sync pattern detection circuit 234.

The reception register 236 stores the reception data demodulated by the demodulation circuit 235. The error detection circuit 237 performs error detection on reception data, and outputs the result to the reception control circuit 231.

Upon receipt of a result notification from the error detection circuit 237, the reception control circuit 231 outputs to the transmitter 22 information to the effect that an acknowledge signal has been received if no error was detected in the reception data and a code indicating an acknowledge signal was present in a specific region of the reception data, and otherwise outputs information to the effect that there was no acknowledge signal, and ends the reception operation. The reception control circuit 231 also ends the reception operation when a reception end signal has been received from the transmitter 22.

Storage Component 24

Figure 9:
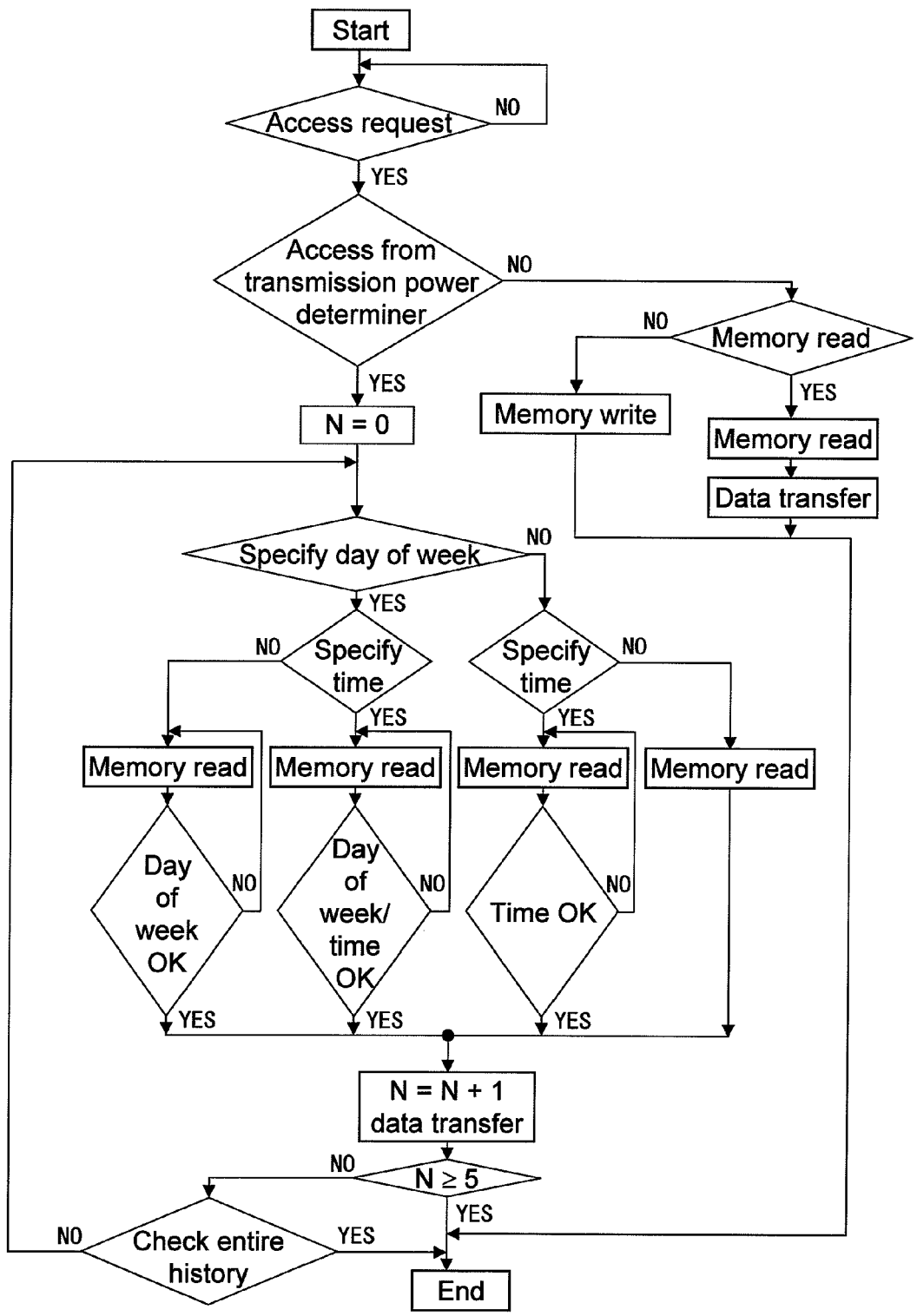
FIG. 9 is a control flowchart of the storage component in the first embodiment of the present invention.

Next, the storage component 24 will be described in detail through reference to FIG. 7, which is a block diagram of the storage component 24, the transmission power and the blood glucose level storage format shown in FIG. 8, and the storage component 24 control flowchart of FIG. 9.

Figure 7:
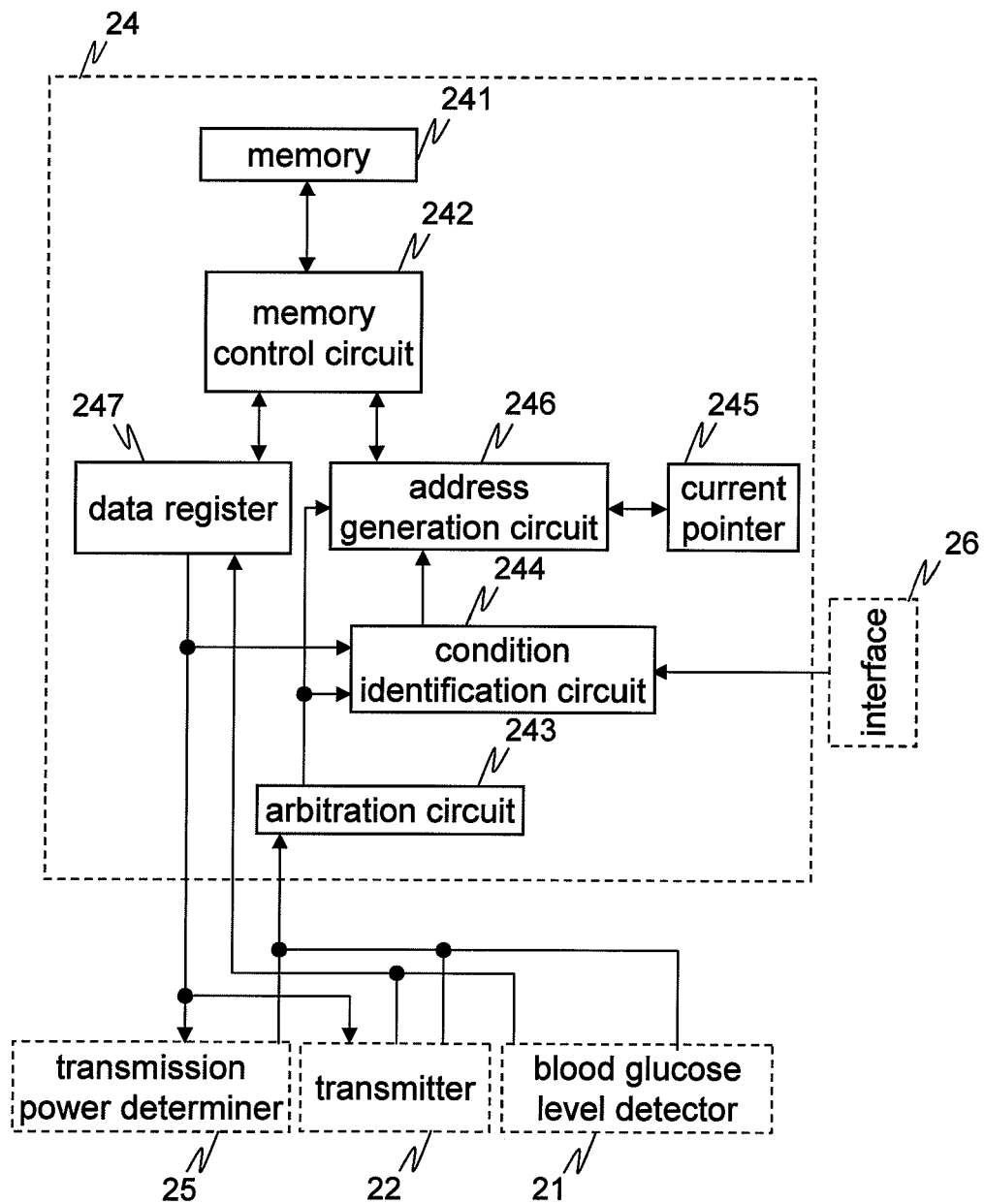
FIG. 7 is a block diagram of a storage component in the first embodiment of the present invention.

As shown in FIG. 7, the storage component 24 has a memory 241, a memory control circuit 242, an arbitration circuit 243, a condition identification circuit 244, a current pointer 245, an address generation circuit 246, and a data register 247.

As shown in FIG. 7, blocks that read and write data to the storage component 24 include the blood glucose level detector 21, the transmitter 22, and the transmission power determiner 25. Since special access from the transmission power determiner 25 to the storage component 24 is performed, this will be discussed in detail at a later point.

The blood glucose level detector 21 includes parameters necessary for finding a blood glucose level, which are loaded in a nonvolatile memory of the storage component 24 before shipment from the factory. Also, during blood glucose level measurement, parameters loaded before shipment from the factory are read out in order to convert from a voltage value to a blood glucose level.

When blood glucose level data is transmitted, the transmitter 22 loads various information (day of the week, transmission time (h), whether or not an acknowledge signal has been received (ACK), transmission power, and blood glucose level) according to the format shown in FIG. 8.

The arbitration circuit 243 arbitrates a memory access request from the blood glucose level detector 21 and the transmitter 22, and allocates a memory access right to the block that outputted a memory access request. The block to which the memory access right was allocated transfers write data to the storage component 24 if the access direction information (whether it is memory read or memory write) is memory write.

The data register 247 temporarily loads write data and read data to the memory 241.

The memory control circuit 242 produces a control signal for the memory 241. The memory control circuit 242 performs access control with respect to the memory 241 upon supply of access direction information.

The memory 241 is a memory that stores data, such as an EEPROM or a DRAM. Since the parameters for finding a blood glucose level are put in memory before shipment from the factory, the memory 241 comprises either a nonvolatile memory alone, or a nonvolatile memory plus a volatile memory. In the case of memory write access, the write address and write data are outputted to the memory 241 from the address generation circuit 246 and the data register 247, respectively, under control of the memory control circuit 242, and processing is ended at the point when the data is written to the memory 241. Meanwhile, in the case of memory read access, the data read out from the memory 241 is temporarily stored in the data register 247. The read data stored in the data register 247 is transferred to the block subject to memory access, and memory read processing ends.

If the memory access to the memory 241 is memory write from the transmitter 22, for example, then after the day of the week, the transmission time (h), whether or not an acknowledge signal has been received, transmission power, and blood glucose level data are written to the address indicated by the current pointer 245 of the memory 241, the value of the current pointer 245 is increased by 4 bytes. If the value of the current pointer 245 indicated the head of the DATA 255 in FIG. 8 before the current pointer 245 was increased by 4, then the value of the current pointer 245 is changed to a value indicating the head of DATA0.

Next, the operation will be described for when the transmission power determiner 25 reads data from the storage component 24.

A memory access request signal from the transmission power determiner 25 to the storage component 24 is arbitrated by the arbitration circuit 243. If a memory access right is granted to the transmission power determiner 25, the condition identification circuit 244 performs data extraction by searching, in the reverse order from that stored in the storage component 24 (that is, starting from the most recent point), on the basis of the extraction conditions (transmission power determination rule) inputted at the interface 26. More specifically, for example, if the extraction conditions are set so that history information is extracted for the same day of the week and the same time period as the current measurement time, the condition identification circuit 244 decides whether it is data for the same day of the week as that at the time of use, data for the same time period, data that is unrelated to the day of week or time period, or data for the same day of the week and the same time period.

Here, history information is extracted on the basis of the empirical rule that it is most likely that on a given day of the week or at a given time period, the user will generally use the wireless blood glucose meter 2 in the same place, that is, in the same environment. Consequently, the transmission power in transmission by the transmitter can be determined according to the usage environment.

The transmission power determiner 25 then continues memory access to the storage component 24 until five sets of history information matching the extraction conditions have been found, or until all of the history information has been checked.

The address generation circuit 246 stores the current value of the current pointer 245 once access of the transmission power determiner 25 starts, after which a four-byte address is outputted as a memory address to the memory control circuit 242 from the value indicated by the current pointer 245 in the direction of decreasing addresses, for each memory address.

The memory control circuit 242 reads four bytes of data from the memory 241 by using the memory address received from the address generation circuit 246. The data that is read out is stored in the data register 247.

The condition identification circuit 244 analyzes the data stored in the data register 247, and determines whether or not it matches the history conditions received from the interface 26. If there are fewer than five sets of data matching the history conditions, the condition identification circuit 244 repeats memory read while subtracting four bytes at a time from the value of the memory current pointer 245 that manages the address of the memory storing information related to transmission data. However, once all of the history information has been read, access is ended even though there are fewer than five sets of data matching the history conditions. When access is ended, the value of the current pointer 245 is returned to the value that was stored at the start of access.

Transmission Power Determiner 25

Next, the transmission power determiner 25 will be described in detail through reference to FIG. 10, which is a block diagram of the transmission power determiner 25, and FIG. 11, which is a control flowchart for the transmission power determiner 25.

Figure 10:
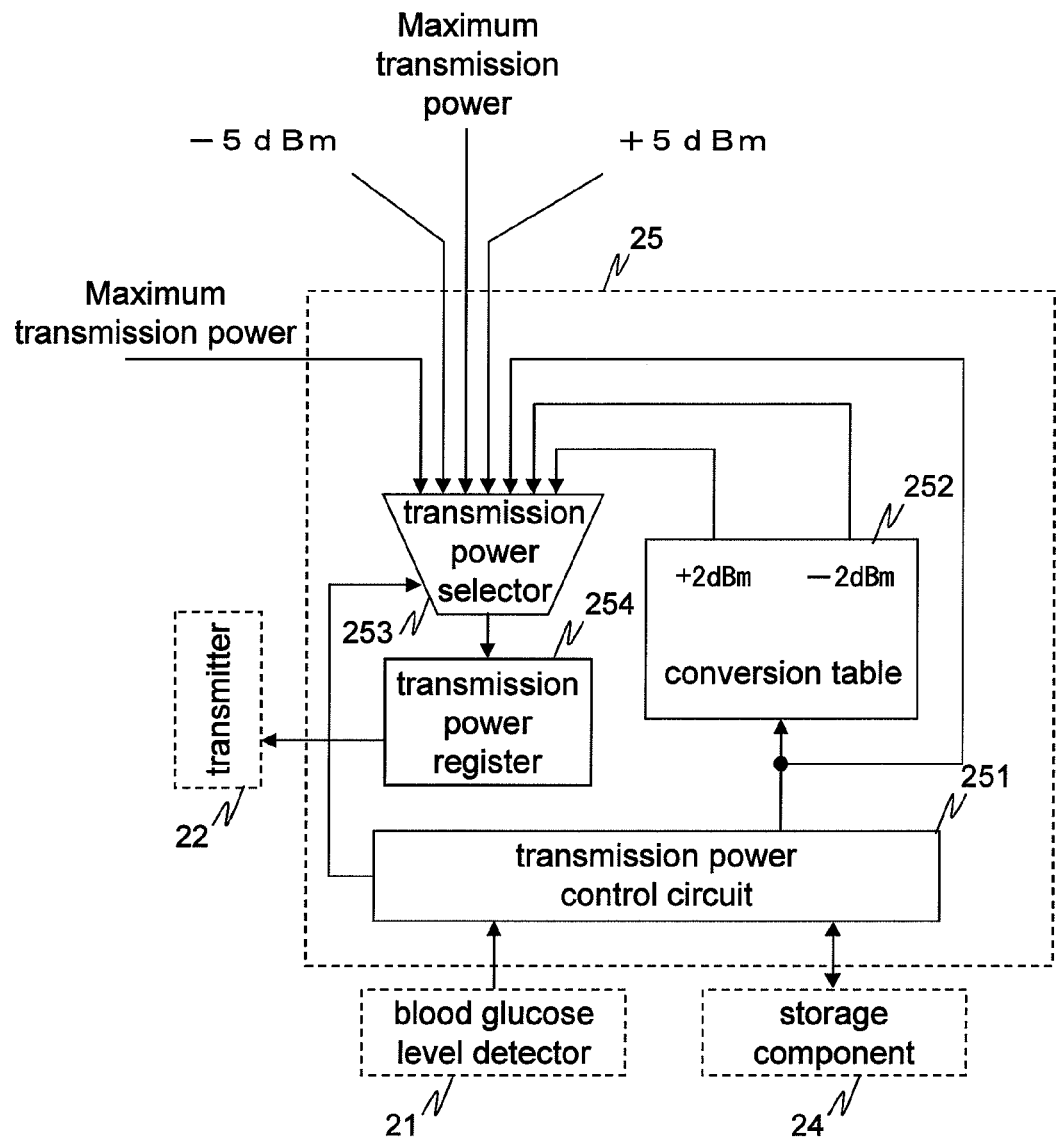
FIG. 10 is a block diagram of a transmission power determiner in the first embodiment of the present invention.

As shown in FIG. 10, the transmission power determiner 25 comprises a transmission power control circuit 251, a conversion table 252, a transmission power selector 253, and a transmission power register 254.

The transmission power control circuit 251 controls the conversion table 252 and the transmission power control circuit 251.

The conversion table 252 outputs a power value that is 2 dBm greater than or 2 dBm less than the power outputted by the transmission power control circuit 251.

The transmission power selector 253 switches the transmission power stored in the transmission power register 254.

The transmission power register 254 outputs the transmission power stored as the optimal power to the transmitter 22.

Figure 11:
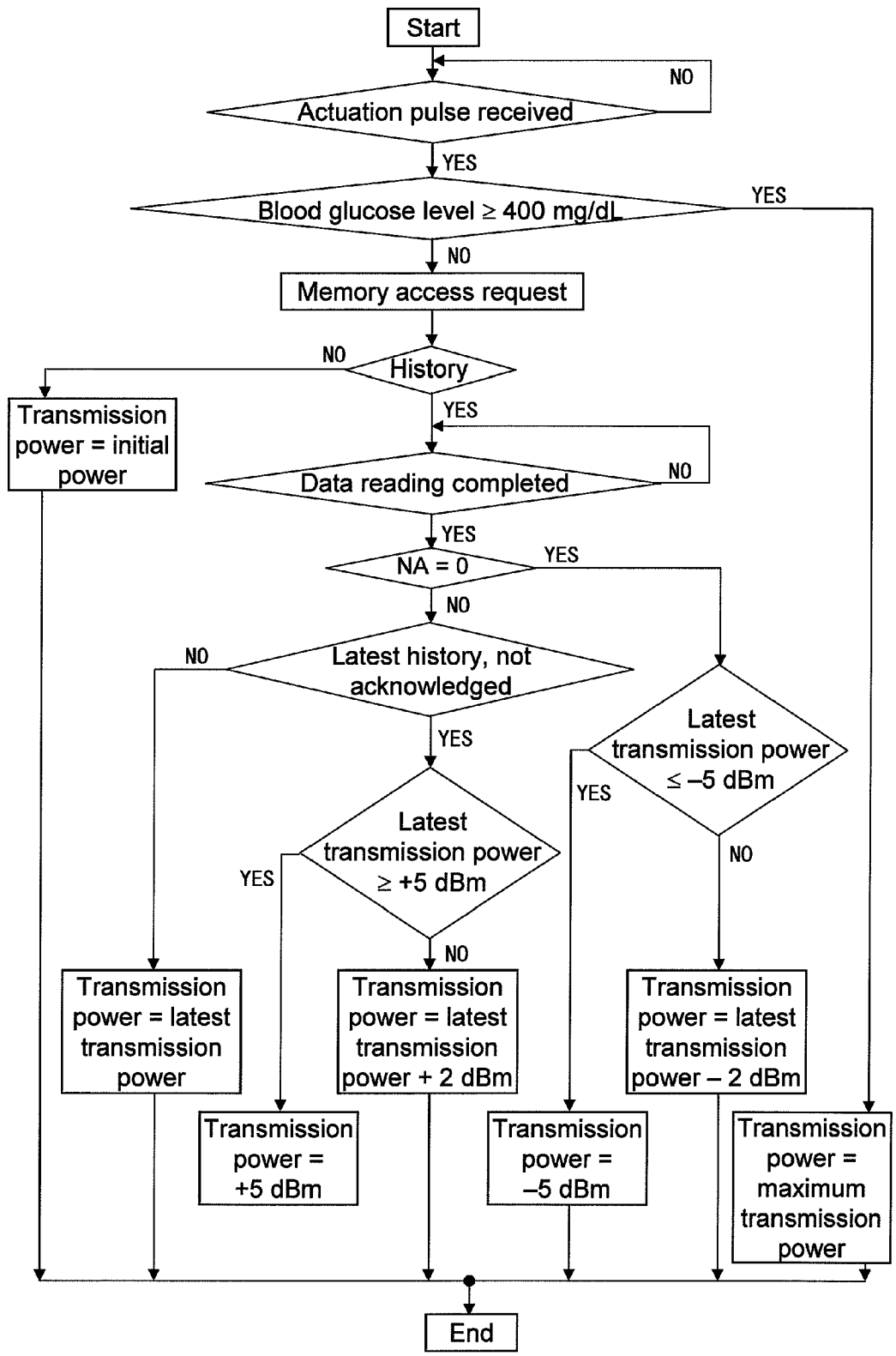
FIG. 11 is a control flowchart of the transmission power determiner in the first embodiment of the present invention.

"NA" in the control flowchart of FIG. 11 indicates a count value indicating the number of pieces of history information for which there was no receipt of an acknowledge signal in the history information read out from the storage component 24.

The transmission power control circuit 251 checks whether the blood glucose level is at least 400 mg/dl when blood glucose level data and an actuation pulse are outputted from the blood glucose level detector 21.

If the blood glucose level is at least 400 mg/dL, the transmission power control circuit 251 switches the transmission power selector 253 and stores the maximum transmission power in the transmission power register 254. The transmission power register 254 then outputs the maximum transmission power stored as the optimal power to the transmitter 22. This makes it possible to minimize the loss of transmission due to insufficient transmission power in situations where urgent care by a physician or the like is necessary.

Meanwhile, if the blood glucose level is less than 400 mg/dL, the transmission power control circuit 251 sends a memory access request to the storage component 24. When the memory access request is received by the storage component 24, and history information is transferred as read data from the storage component 24 to the transmission power control circuit 251, the transmission power control circuit 251 checks whether the history information includes information about whether or not an acknowledge signal has been received, and counts the number without receipt of an acknowledge signal in the received history information as NA (NO ACK).

If NA is zero, an acknowledge signal has been received for all of the extracted history information, so it is possible that the transmission power is higher than necessary. Therefore, if the most recent transmission power included in the history information (latest transmission power) is not equal to or lower than the −5 dBm specified as the minimum power (indicating that the initial power minus 5 dBm), the transmission power control circuit 251 will switch the transmission power selector 253 so that a value that is 2 dBm less than the latest transmission power is outputted, and store this in the transmission power register 254. On the other hand, if the latest transmission power is equal to or lower than the −5 dBm specified as the minimum power, the transmission power control circuit 251 will switch the transmission power selector 253 so as to output at the −5 dBm specified as the minimum power, and store this in the transmission power register 254.

Consequently, the transmission power in transmission by the transmitter 22 can be reduced while still allowing communication between the portable terminal 3 and the wireless blood glucose meter 2, thus achieving a power saving.

If NA is 1 or higher and an acknowledge signal has not been received for the most recent history information (labeled in FIG. 11 as "Latest history, not acknowledged"), it is possible that the transmission power is lower than the required power. Therefore, if the most recent transmission power included in the history information is not at least the +5 dBm specified as the maximum power (indicating that the initial power plus 5 dBm), the transmission power control circuit 251 will switch the transmission power selector 253 so that a value that is 2 dBm greater than this transmission power is outputted, and store this in the transmission power register 254. On the other hand, if the most recent transmission power included in the history information is at least the +5 dBm specified as the maximum power, the transmission power control circuit 251 will switch the transmission power selector 253 so as to output at the +5 dBm specified as the maximum power, and store this in the transmission power register 254.

Also, if NA is at least 1 and an acknowledge signal has been received for the most recent history information, the transmission power selector 253 selects the power outputted by the transmission power control circuit 251 so that the most recent transmission power included in the history information will be stored in the transmission power register 254.

Consequently, the transmission power in transmission by the transmitter 22 can be determined more optimally so that the data sent from the wireless blood glucose meter 2 can be properly received by the portable terminal 3.

Thus, whether to raise or lower the transmission power is determined by whether or not an NA is included in the latest five sets of history information among the extraction conditions. The transmission power selector 253 selects the initial power when the user begins to use the wireless blood glucose meter 2, or when no history information has been stored in the storage component 24 due to software resetting or the like. The "initial power" here is enough power for radio waves to reach, assuming normal use, and is, for example, an intermediate value between the maximum transmission power and the minimum transmission power at which communication is possible.

The transmission power register 254 then outputs the power stored as the optimal power to the transmitter 22.

Interface 26

Figure 12:
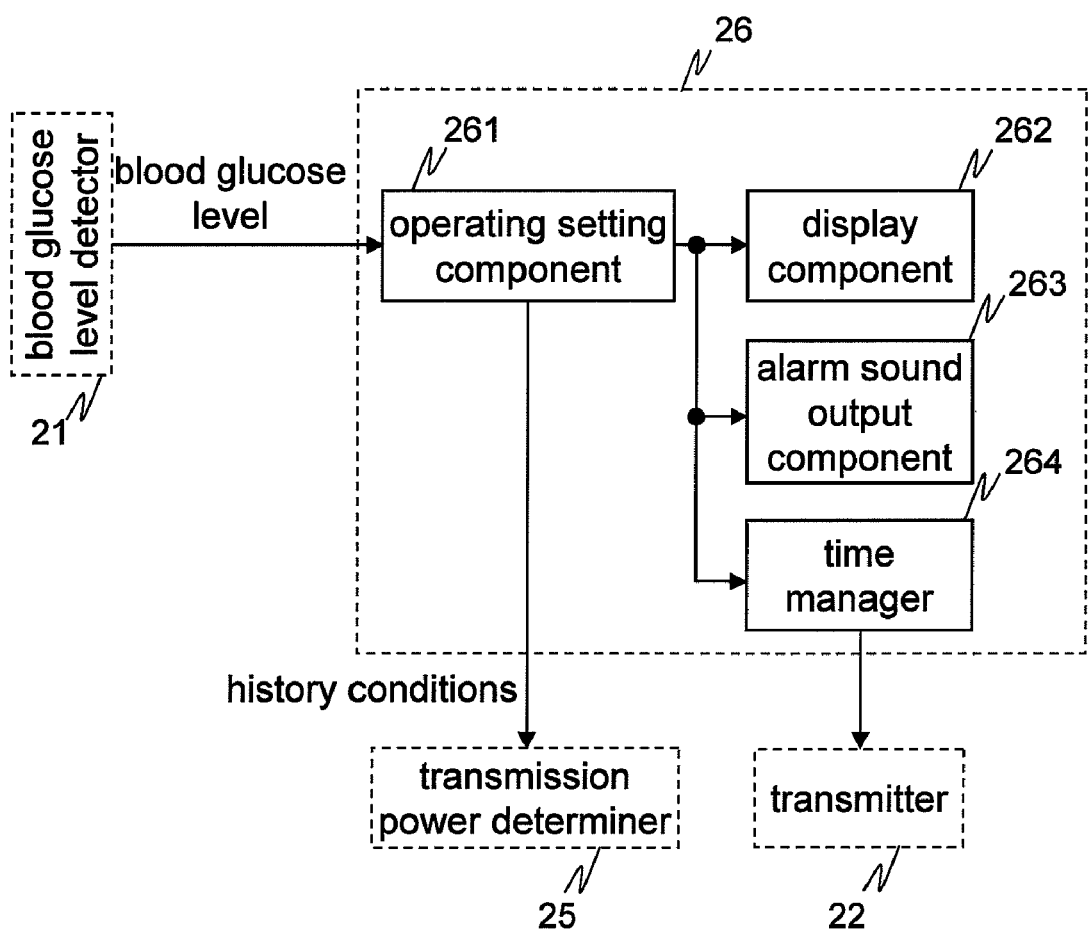
FIG. 12 is a block diagram of an interface in the first embodiment of the present invention.

Next, the interface 26 will be described in detail through reference to FIG. 12, which is a block diagram of the interface 26.

The user adjusts the settings by using the operating setting component 261 while checking the setting categories displayed on the display component 262. The setting categories here include the day of the week, the time, the history conditions for determining the transmission power (setting whether to use data for the same day of the week, data for the same time period, data that is unrelated to the day of week or time period, or data for the same day of the week and the same time period as the history information), and other such information.

The history conditions set with the operating setting component 261 are outputted to the transmission power determiner 25. Meanwhile, the day of the week and time are outputted to a time manager 264.

The time manager 264 manages the current day of the week and time along with the setting information. The information about day of the week and time managed in the time manager 264 is outputted to the transmitter 22.

When a blood glucose level is calculated by the blood glucose level detector 21, the display component 262 displays the calculated blood glucose level. If the calculated blood glucose level is 50 mg/dL or less, the user (diabetes patient) is in an extremely dangerous situation, so the alarm sound output component 263 outputs an alarm sound in order to alert any people around the user to this danger. It is conceivable that the user may have lost consciousness, so the display component 262 displays an emergency contact telephone number or information related to emergency measures, such as ingesting sugar.

Consequently, people around the user of the wireless blood glucose meter 2 can be alerted that the user remains in critical condition. Also, even if the user of the wireless blood glucose meter 2 should lose consciousness, a nearby person can see the telephone number displayed on the display component 262 and immediately call the emergency contact number, or can provide suitable assistance while looking at the treatment method, etc., displayed on the display component 262.

Second Embodiment

The wireless blood glucose meter 2 in another embodiment of the present invention will now be described through reference to FIGS. 13 to 17. This embodiment differs from the first embodiment in that a noise power acquisition component (noise power measurement component) 28 is provided to calculate the transmission power in transmission by the transmitter 22, and the noise power measured in the noise power acquisition component 28 is also taken into account. Thus, the parts that are in common with the first embodiment will not be described again, and only the control flow of the receiver 23, the format of data storage in the memory 241, and the transmission power determiner 25 that are different from the first embodiment will be described in detail.

Receiver 23

The differences from the receiver 23 in the first embodiment will be described through reference to FIG. 13, which is a block diagram of the receiver 23, and FIG. 14, which is a control flowchart for the receiver 23.

Figure 13:
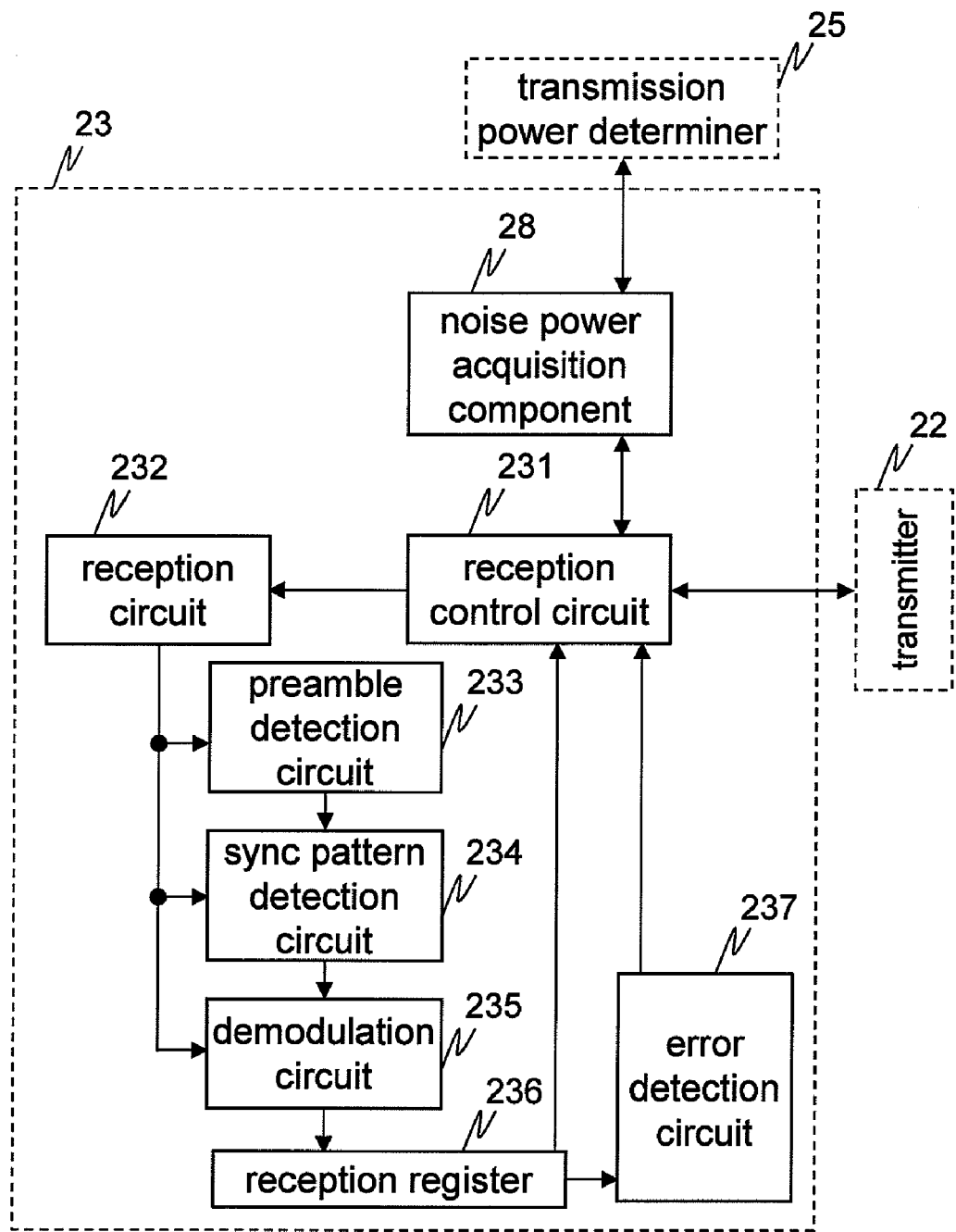
FIG. 13 is a block diagram of the receiver in a second embodiment of the present invention.

In FIG. 13, the noise power acquisition component 28 for receiving noise is added to the first embodiment (see FIG. 5).

The noise power acquisition component 28 acquires the noise power around where the noise power acquisition component 28 is installed, and outputs it to the transmitter 22.

Consequently, the effect of noise power can be taken into account in determining the transmission power in transmission by the transmitter 22.

Figure 6:
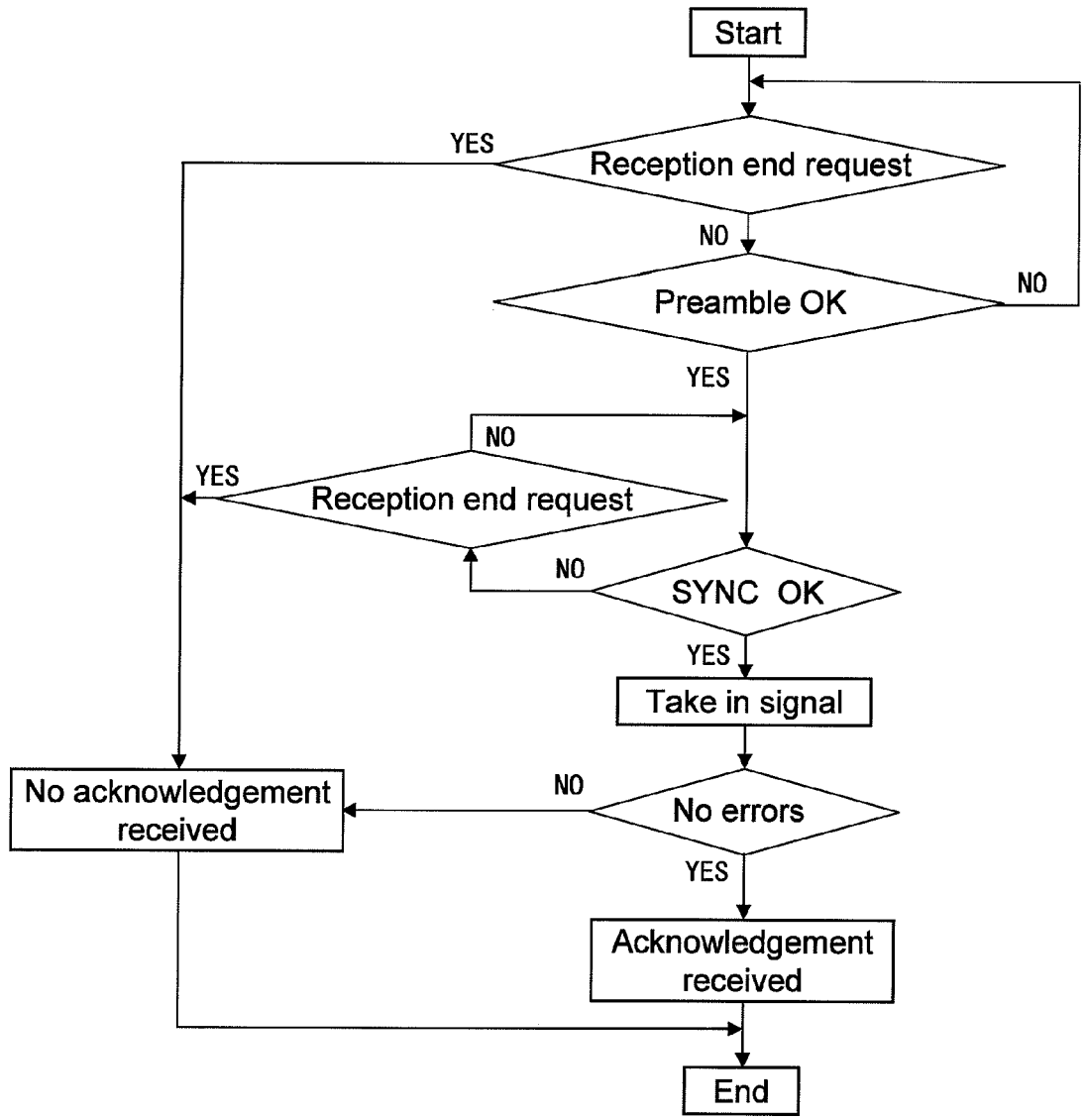
FIG. 6 is a control flowchart of the receiver in the first embodiment of the present invention.
Figure 14:
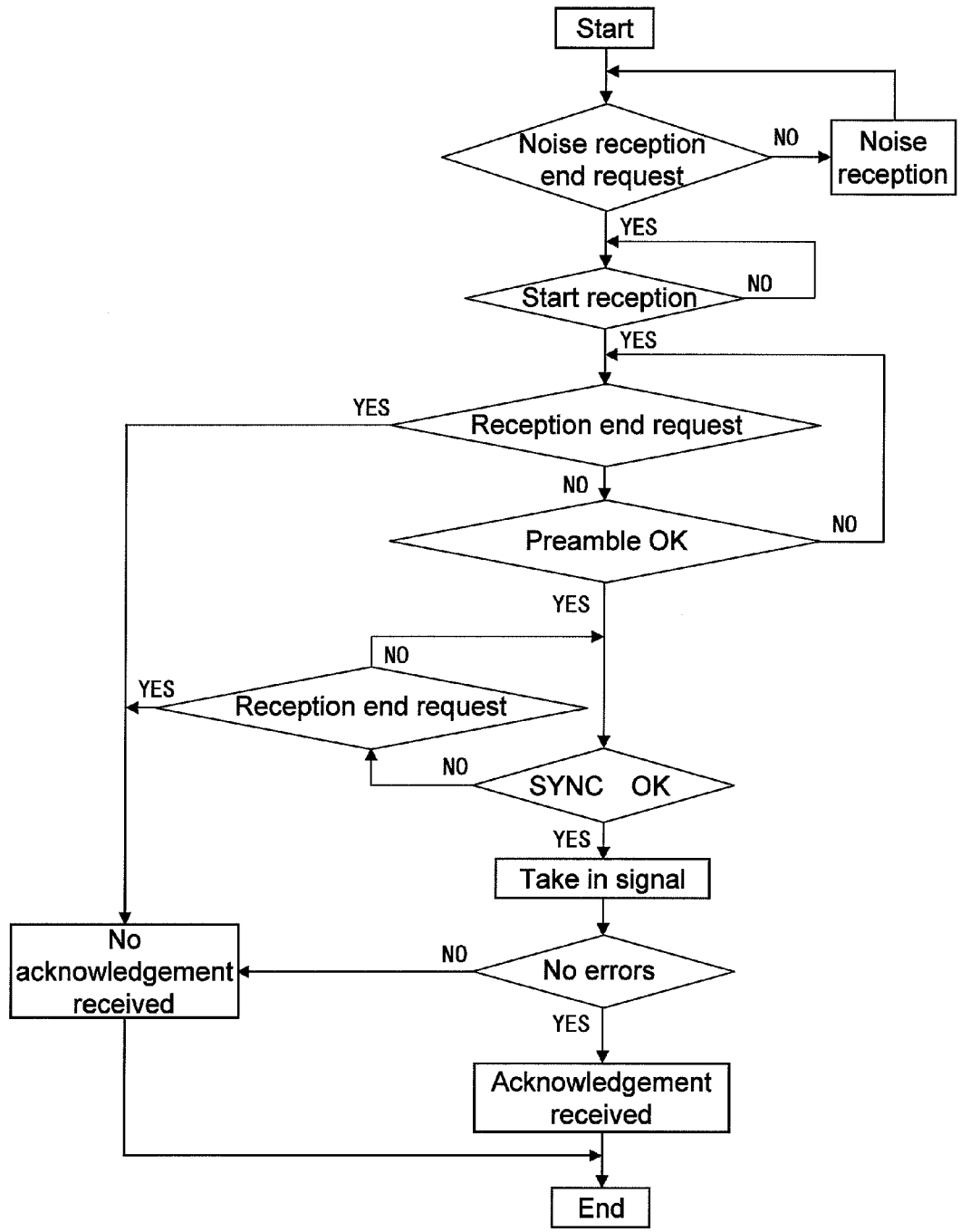
FIG. 14 is a control flowchart of the receiver in the second embodiment of the present invention.

In FIG. 14, a control flow for receiving noise is newly added to the first embodiment (see FIG. 6).

First, the reception control circuit 231 starts the operation of the noise power acquisition component 28 under a noise reception start command from the transmission control circuit 221. The noise power acquisition component 28 measures the reception power in the frequency band used for communication. The reception control circuit 231 stops the operation of the noise power acquisition component 28 when a noise reception end command is inputted from the transmission control circuit 221. Then, the noise power acquisition component 28 sends the received noise power to the transmission power determiner 25.

Storage Component 24

The difference in the storage component 24 from that in the first embodiment (see FIG. 8) is that noise power is stored in the memory 241 as shown in FIG. 15.

Transmission Power Determiner 25

The differences of the transmission power determiner 25 from that in the first embodiment will be described through reference to FIG. 16, which is a block diagram of the transmission power determiner 25, and FIG. 17, which is a control flowchart for the transmission power determiner 25.

Figure 16:
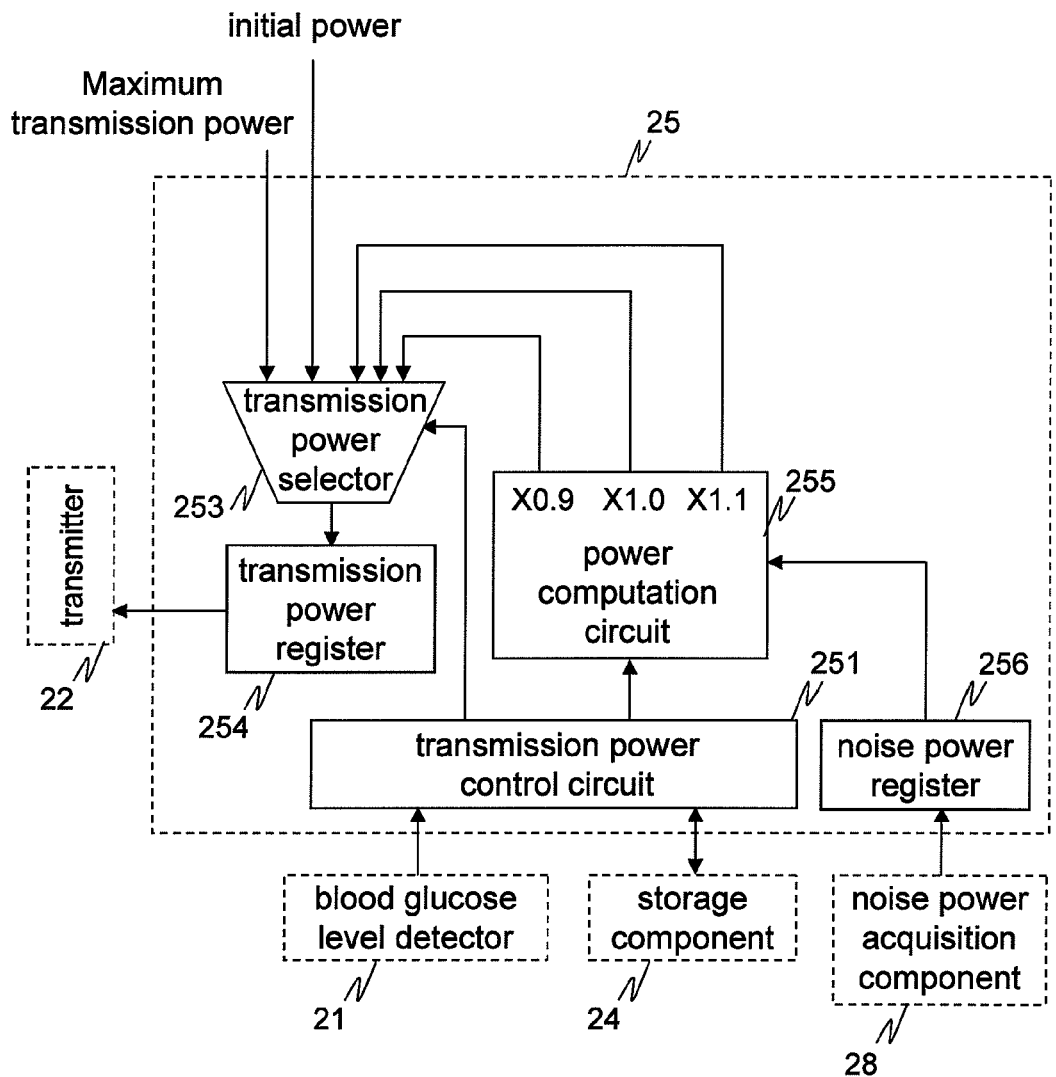
FIG. 16 is a block diagram of the transmission power determiner in the second embodiment of the present invention.
Figure 17:
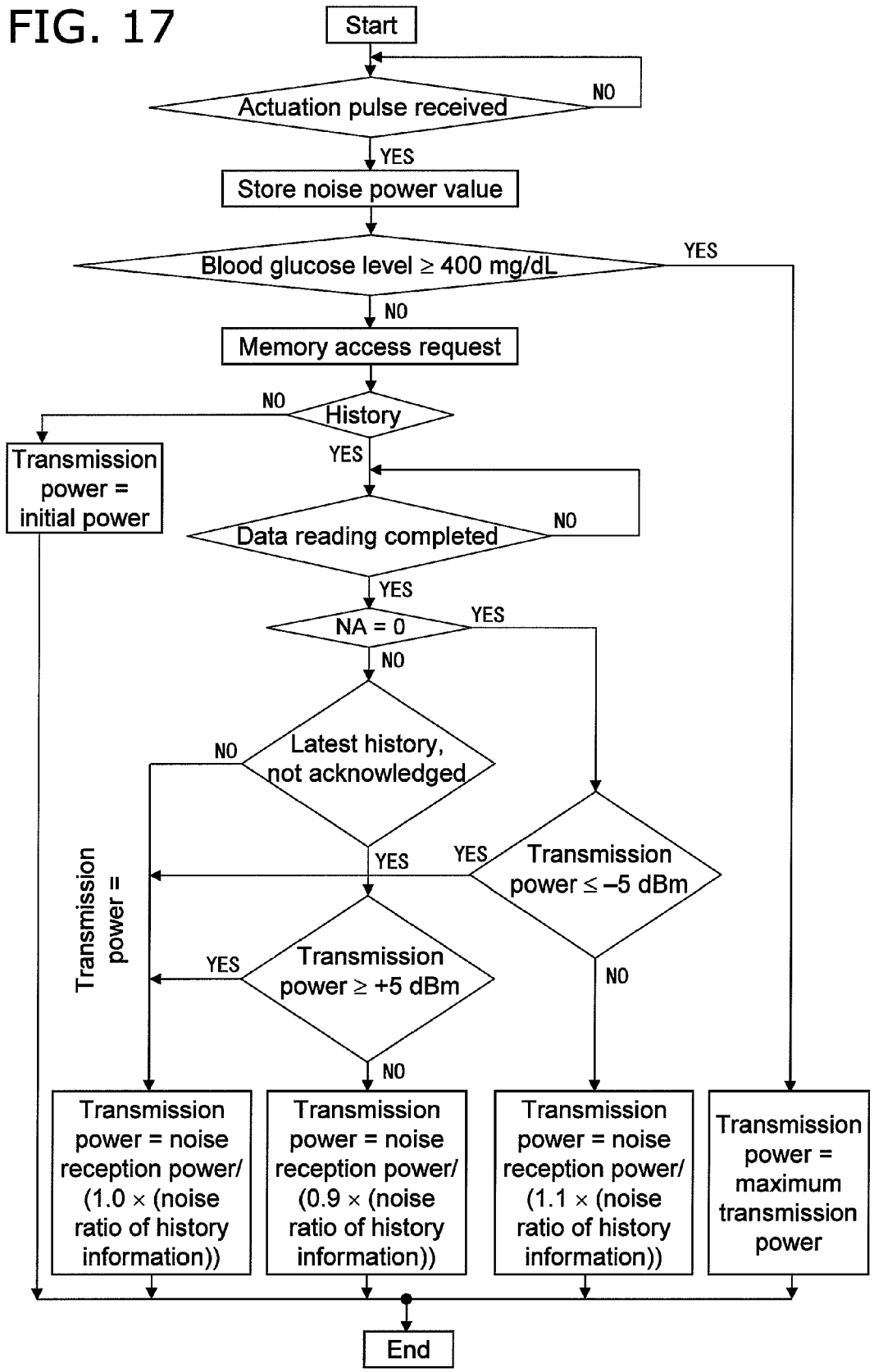
FIG. 17 is a control flowchart of the transmission power determiner in the second embodiment of the present invention.

In FIG. 16, the conversion table 252 is deleted from the first embodiment (see FIG. 10), and a power computation circuit 255 that calculates the optimal power and a noise power register 256 that stores the noise power outputted from the noise power acquisition component 28 are added.

When blood glucose level data and an actuation pulse are outputted from the blood glucose level detector 21, the noise power outputted from the noise power acquisition component 28 is stored in the noise power register 256. Next, the transmission power control circuit 251 checks whether the blood glucose level is at least 400 mg/dL.

If the blood glucose level is at least 400 mg/dL, there is an urgent need for treatment by a physician or the like, so the transmission power register 254 switches the transmission power selector 253 and outputs the maximum transmission power as the optimal power to the transmitter 22.

On the other hand, if the blood glucose level is less than 400 mg/dL, the transmission power control circuit 251 sends a memory access request to the storage component 24. When a memory access request is received by the storage component 24, history information is transferred as read data from the storage component 24 to the transmission power control circuit 251.

If we let the ratio of noise power to transmission power be the noise ratio (the inverse of the S/N ratio), the power computation circuit 255 outputs power so that the noise ratio of the noise power register 256 with respect to the output of the power computation circuit 255 is 0.9 times, 1.0 times, and 1.1 times the noise ratio of the noise power with respect to the transmission power of the most recent history information (labeled as ×0.9, ×1.0, and ×1.1 in FIG. 16). Also, the transmission power control circuit 251 checks whether or not an acknowledge signal receipt is included in the history information, and counts the number where there is no acknowledge signal receipt in the received history information as NA (no acknowledge).

If NA is zero, an acknowledge signal has been received for all of the extracted history information, so it is possible that the transmission power is higher than necessary. Therefore, the transmission power control circuit 251 switches the transmission power selector 253 so that a value that is 1.1 times as calculated by the power computation circuit 255 is stored in the transmission power register 254.

However, it is possible that the data cannot be transmitted properly if the transmission power is too low. Therefore, a lower limit must be set for the transmission power. Here, if the transmission power for the most recent history information is no more than the −5 dBm specified as the minimum power (indicating that the initial power was −5 dBm), to keep the transmission power from being even lower than this, the transmission power control circuit 251 switches the transmission power selector 253 so that a value that is 1.0 times as calculated by the power computation circuit 255 is stored in the transmission power register 254.

Consequently, the transmission power in transmission by the transmitter 22 can be reduced while still allowing communication between the portable terminal 3 and the wireless blood glucose meter 2, thus achieving a power saving.

If NA is 1 or higher and an acknowledge signal has not been received for the most recent history information (labeled in FIG. 17 as "Latest history, not acknowledged"), it is possible that the transmission power is lower than the required power. Therefore, the transmission power control circuit 251 switches the transmission power selector 253 so that a value that is 0.9 times as calculated by the power computation circuit 255 is stored in the transmission power register 254.

However, it is possible that the data cannot be transmitted properly even if the transmission power is raised. If this should happen, it is undesirable for the transmission power to be raised too high. Therefore, an upper limit is set for the transmission power. Here, if the transmission power for the most recent history information is at least the +5 dBm specified as the maximum power (indicating that the initial power was +5 dBm), to keep the transmission power from being even higher than this, the transmission power control circuit 251 switches the transmission power selector 253 so that a value that is 1.0 times as calculated by the power computation circuit 255 is stored in the transmission power register 254.

Consequently, the transmission power in transmission by the transmitter 22 can be determined more optimally so that the data sent from the wireless blood glucose meter 2 can be received by the portable terminal 3.

In a case other than the above, specifically, if an acknowledge signal has been received for the most recent history information at an NA of 1 or more, the transmission power control circuit 251 switches the transmission power selector 253 so that a value of 1.0 times as calculated by the power computation circuit 255 is stored in the transmission power register 254. Consequently, the optimal transmission power is supplied to the transmitter 22. If no history information has been stored in the storage component 24, the selection of the initial power is the same as in FIG. 10.

Third Embodiment

A blood glucose level measurement system (biological sample measurement system) 4 pertaining to an embodiment of the present invention will now be described through reference to FIGS. 18 to 21. This embodiment differs from the first embodiment in that the reception power in data reception by a portable terminal (external device) 3 from a wireless blood glucose meter 2 is included in the acknowledge signal sent from the portable terminal 3 to the wireless blood glucose meter 2. Accordingly, differences from the first embodiment are the format of the data stored in the memory 241 of the storage component 24, the method for accessing this memory 241, and the method for determining the transmission power. These points will be described in detail, but the rest of the constitution and operation that are the same as in the first embodiment will not be described again.

First, the acknowledge signal sent from the portable terminal 3 and received by the receiver 23 is composed of status information and the reception power when data is received by the portable terminal 3.

The transmitter 22 sends blood glucose level data to the portable terminal 3, after which the storage component 24 is instructed to store various information (day of the week, transmission hour (time), transmission power, whether or not an acknowledge signal has been received (ACK), reception power in reception by the portable terminal 3, reference reception power, and blood glucose level) according to the format shown in FIG. 18. The reference reception power will be discussed below.

Next, the transmission power determiner 25 will be described in detail through reference to FIG. 19, which is a block diagram of the transmission power determiner 25, and FIG. 20, which is a control flowchart for the transmission power determiner 25.

Figure 19:
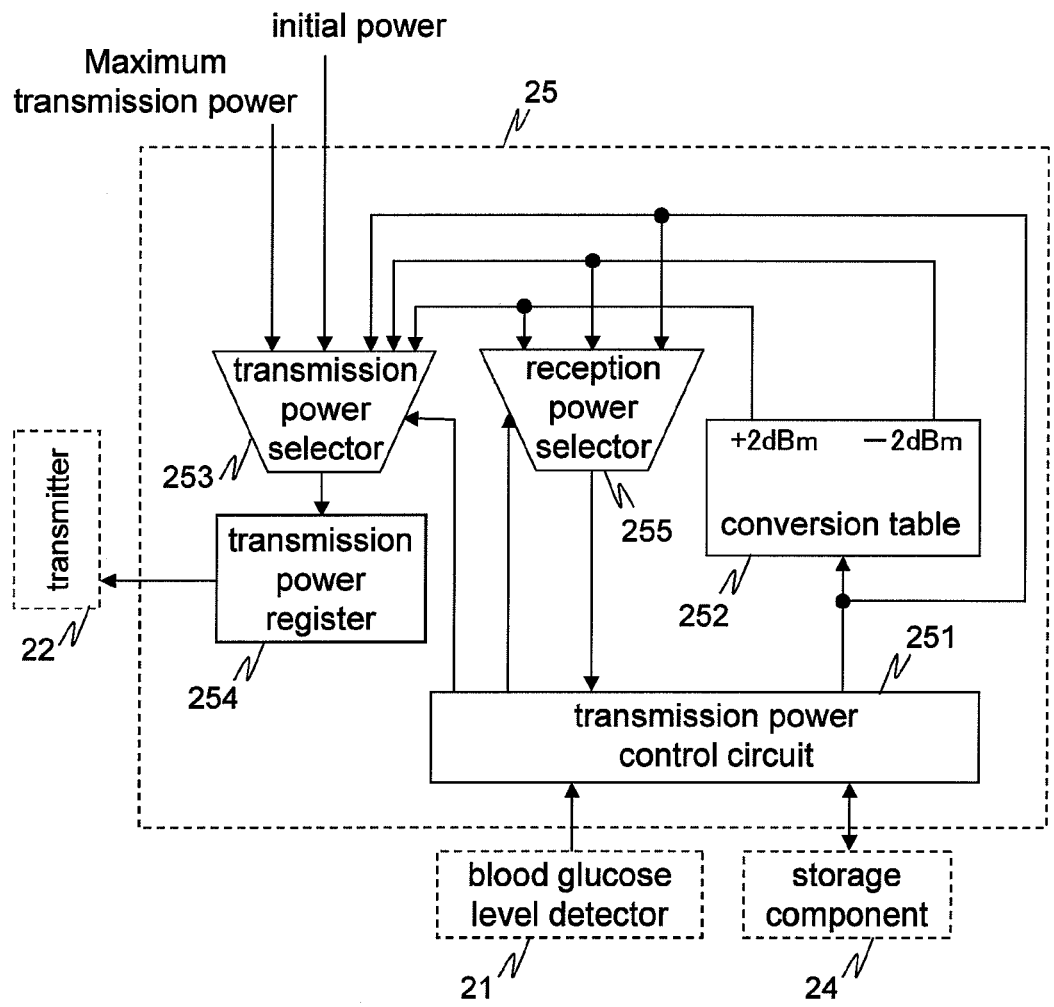
FIG. 19 is a block diagram of the transmission power determiner in the third embodiment of the present invention.

As shown in FIG. 19, the transmission power determiner 25 comprises a transmission power control circuit 251, a conversion table 252, a transmission power selector 253, a transmission power register 254, and a reception power selector 255.

The transmission power control circuit 251 controls the conversion table 252 and the transmission power control circuit 251.

The conversion table 252 outputs a power value that is 2 dBm greater than or 2 dBm less than the power outputted by the transmission power control circuit 251.

The transmission power selector 253 switches the transmission power stored in the transmission power register 254.

The transmission power register 254 outputs the transmission power stored as the optimal power to the transmitter 22.

The reception power selector 255 switches the reference reception power set as the optimal reception power when the portable terminal 3 receives blood glucose level data.

Figure 20:
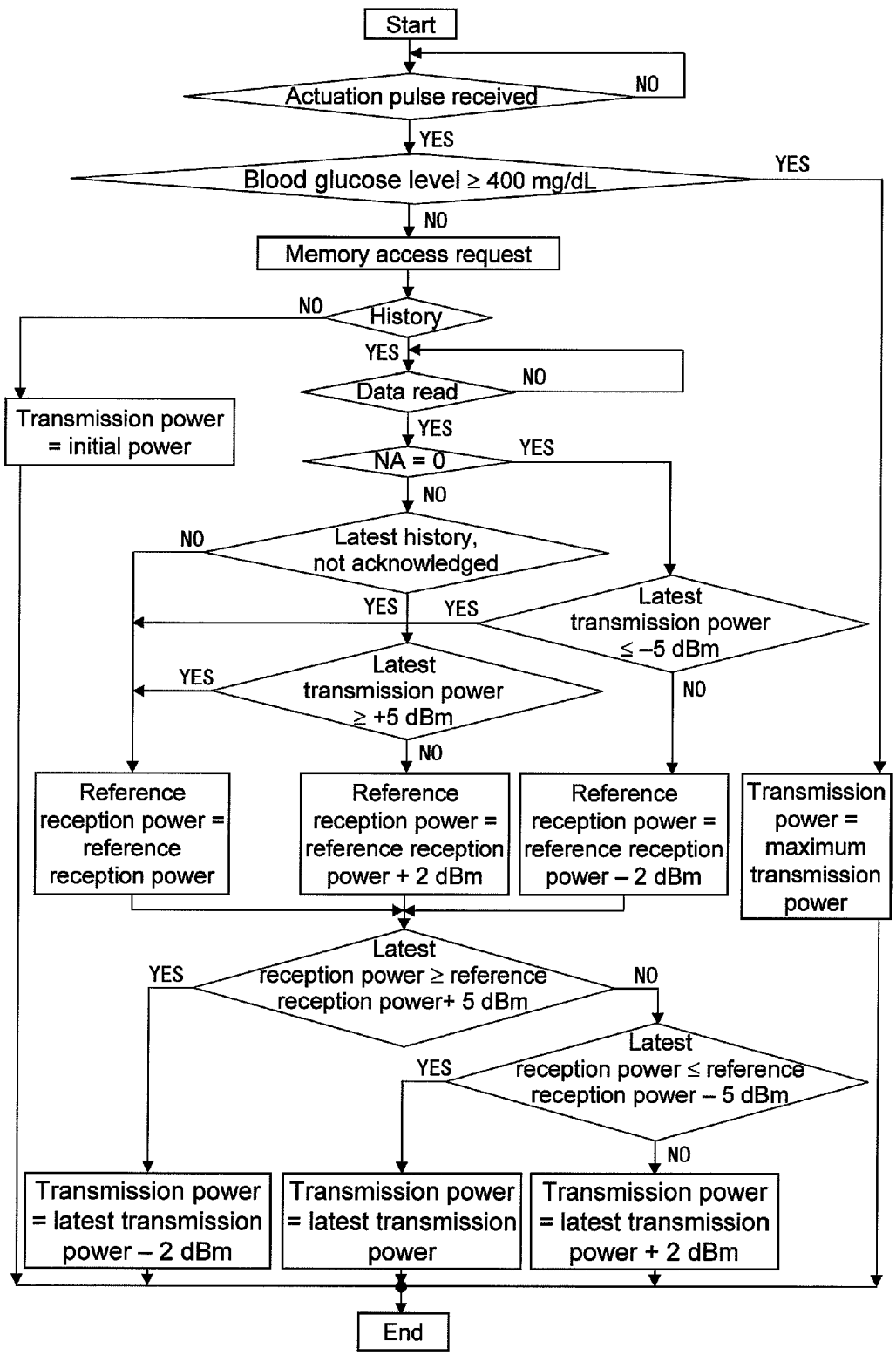
FIG. 20 is a control flowchart of the transmission power determiner in the third embodiment of the present invention.

"NA" in the control flowchart of FIG. 20 indicates a count value indicating the number of pieces of history information for which there was no receipt of an acknowledge signal in the history information read out from the storage component 24.

The transmission power control circuit 251 checks whether the blood glucose level is at least 400 mg/dL when blood glucose level data and an actuation pulse are outputted from the blood glucose level detector 21.

If the blood glucose level is at least 400 mg/dL, the transmission power control circuit 251 switches the transmission power selector 253 and stores the maximum transmission power in the transmission power register 254. The transmission power register 254 then outputs the maximum transmission power stored as the optimal power to the transmitter 22. This makes it possible to minimize the loss of transmission due to insufficient transmission power in situations where urgent care by a physician or the like is necessary.

Meanwhile, if the blood glucose level is less than 400 mg/dL, the transmission power control circuit 251 sends a memory access request to the storage component 24. When the memory access request is received by the storage component 24, and history information is transferred as read data from the storage component 24 to the transmission power control circuit 251, the transmission power control circuit 251 checks whether the history information includes information about whether or not an acknowledge signal has been received, and counts the number without receipt of an acknowledge signal in the received history information as NA (no acknowledge).

If NA is zero, an acknowledge signal has been received by the receiver 23 for all of the extracted history information, so it is possible that the reception power when the portable terminal 3 receives blood glucose level data (hereinafter referred to as the reference reception power) is higher than necessary. Therefore, the transmission power control circuit 251 inputs the reference reception power to the conversion table 252, and if the most recent transmission power included in the history information (latest transmission power) is not equal to or lower than the −5 dBm specified as the minimum power (indicating that the initial power was −5 dBm), the transmission power control circuit 251 will switch the reception power selector 255 so that a value that is 2 dBm less than the reference reception power is calculated as a new reference reception power, and store this in the storage component 24. On the other hand, if the latest transmission power is equal to or lower than the −5 dBm specified as the minimum power, the transmission power control circuit 251 will switch the reception power selector 255 so as to output at the current reference reception power, and store this in the storage component 24.

If NA is 1 or higher and an acknowledge signal has not been received for the most recent history information (labeled in FIG. 20 as "Latest history, not acknowledged"), it is possible that the reference reception power is lower than the required power. Therefore, the transmission power control circuit 251 inputs the reference reception power to the conversion table 252, and if the latest transmission power is not at least the +5 dBm specified as the maximum power (indicating that the initial power was +5 dBm), the transmission power control circuit 251 will switch the reception power selector 255 so that a value that is 2 dBm greater than the reference reception power is calculated as a new reference reception power, and store this in the storage component 24. On the other hand, if the latest transmission power is at least the +5 dBm specified as the maximum power, the transmission power control circuit 251 will switch the reception power selector 255 so as to output at the current reference reception power, and store this in the storage component 24.

When the reference reception power is calculated, the transmission power control circuit 251 compares the reference reception power with the reception power for the most recent history information (latest reception power). If the latest reception power is at least 5 dBm greater than the newly calculated reference reception power, the transmission power control circuit 251 inputs the transmission power for the history information to the conversion table 252 and switches the transmission power selector 253 so that a value that is 2 dBm less than the latest transmission power is calculated as a new transmission power, and stores this in the transmission power register 254.

The transmission power register 254 then outputs the power stored as the optimal power to the transmitter 22.

Consequently, the transmission power in transmission by the transmitter 22 can be reduced while still allowing communication between the portable terminal 3 and the wireless blood glucose meter 2, thus achieving a power saving.

Also, if the latest reception power is at least 5 dBm less than the newly calculated reference reception power, the transmission power control circuit 251 inputs the transmission power for the history information to the conversion table 252 and switches the transmission power selector 253 so that a value that is 2 dBm greater than the latest transmission power is calculated as a new transmission power, and stores this in the transmission power register 254.

Also, if the latest reception power is not more than 5 dBm greater and not more than 5 dBm less than the newly calculated reference reception power, that is, if the latest reception power is within a range of ±5 dBm with respect to the newly calculated reference reception power, the transmission power control circuit 251 stores this in the transmission power register 254 without making any changes to the latest transmission power.

The transmission power register 254 then outputs the power stored as the optimal power to the transmitter 22.

Consequently, the transmission power in transmission by the transmitter 22 can be determined optimally so that the data sent by the wireless blood glucose meter 2 can be properly received by the portable terminal 3.

Thus, whether to raise or lower the transmission power is determined by whether or not an NA is included in the latest five sets of history information among the extraction conditions. The transmission power selector 253 selects the initial power when the user begins to use the wireless blood glucose meter 2, or when no history information has been stored in the storage component 24 due to software resetting or the like. The "initial power" here is enough power for radio waves to reach, assuming normal use, and is, for example, an intermediate value between the maximum transmission power and the minimum transmission power at which communication is possible.

Thus, with the wireless blood glucose meter 2 in this embodiment, the reference reception power is set on the basis of the reception power when the portable terminal 3 on the reception side actually receives blood glucose level data, and the transmission power can be determined, so the transmission power can be properly optimized even if the transmission power in transmission by the wireless blood glucose meter 2 and the reception power in reception by the portable terminal 3 are different due to the external environment or the like.

Figure 21:
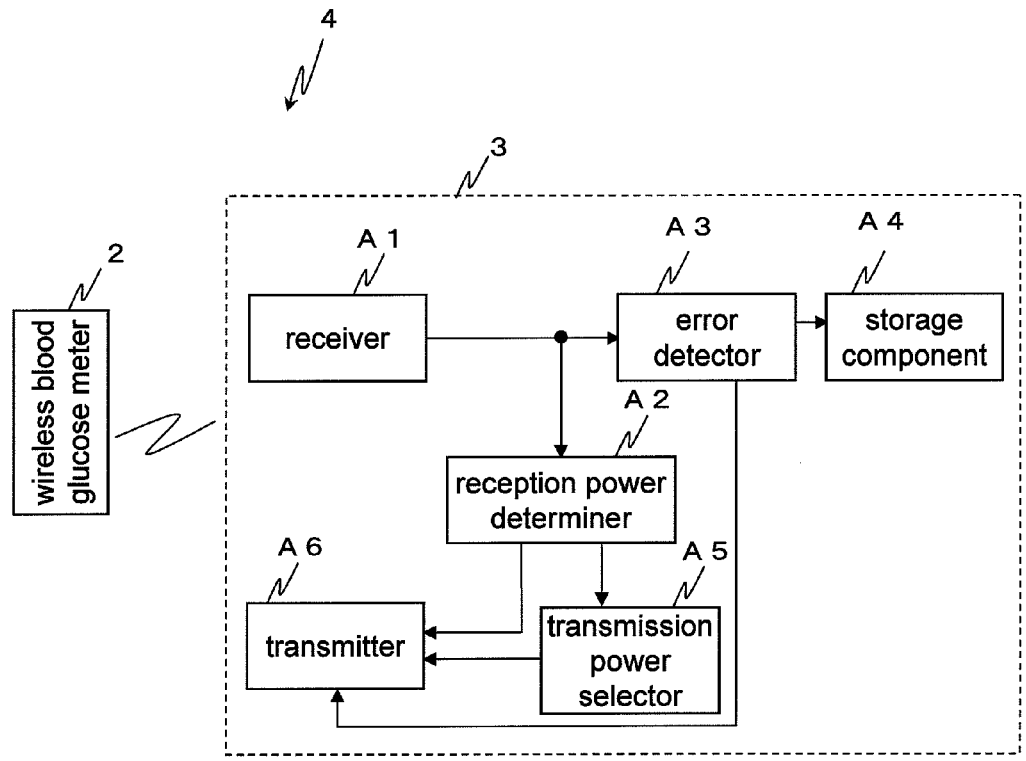
FIG. 21 is a block diagram of the portable terminal in the third embodiment of the present invention.
Figure 22:
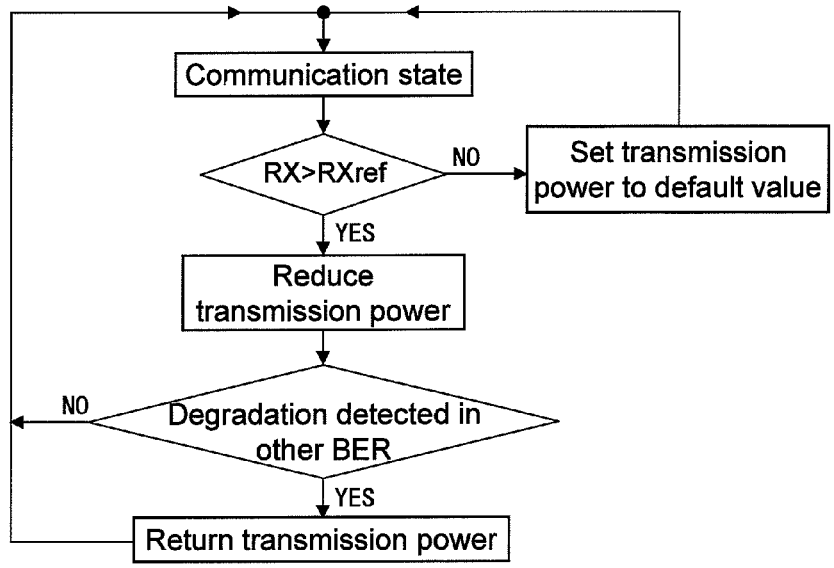
FIG. 22 is a control flowchart of the transmission power with a conventional wireless portable terminal device.

The constitution of the portable terminal 3 will now be described. FIG. 21 is a block diagram of the portable terminal 3. As shown in FIG. 21, the portable terminal 3 has a receiver (external receiver) A1, a reception power determiner A2, an error detector A3, a storage component A4, a transmission power selector A5, and a transmitter (external transmitter) A6.

The receiver A1 detects carrier waves from the received signals, and outputs to the reception power determiner A2. It also uses a preamble pattern or sync pattern of the received signals to demodulate transmission data, and outputs the demodulated data to the error detector A3.

The reception power determiner A2 calculates the reception power in the reception of data by the receiver A1 from the carrier wave outputted from the receiver A1, and compares this with a specific value. The reception power is outputted to the transmitter A6, and the comparison result to the transmission power selector A5. The specific value here is set by the transmission power determiner 25 in the wireless blood glucose meter 2 to a value that is greater than the lower limit power at which the portable terminal 3 can receive, and less than the −5 dBm specified as the minimum power in transmission. Specifically, this specific value is the remainder of subtracting the power that attenuates at the distance between the portable terminal 3 and the wireless blood glucose meter 2 assumed in normal usage from the above-mentioned minimum power (−5 dBm).

The transmission power selector A5 instructs the transmitter A6 to set the transmission power to the maximum power when a result is transmitting indicating that the reception power is below the specific value.

The error detector A3 performs error detection on the demodulated data outputted from the receiver A1 by using an error detection code added to this data. If the result of error detection is that there are no errors, measurement data is taken out of the demodulated data and outputted to the storage component A4. The transmitter A6 is then notified that the measurement data has been properly received.

The storage component A4 stores the measurement data outputted from the error detector A3.

The transmitter A6 sends an acknowledge signal to the wireless blood glucose meter 2 upon being notified that the measurement data has been properly received from the error detector A3. The reception power measured by the reception power determiner A2 is included in this acknowledge signal. If the reception power determiner A2 here has sent out a notification that the reception power is lower than the specific value, transmission is performed at the maximum power at which transmission is possible.

On the other hand, if an error is detected by the error detector A3, the transmitter A6 sends an non-acknowledge signal to the wireless blood glucose meter 2 (interpreted at the wireless blood glucose meter 2 to mean that data transmission was not carried out properly). At this point, transmission is performed at the maximum power at which transmission is possible, regardless of the determination result of the reception power determiner A2.

Thus, if the reception power of the portable terminal 3 is below the specific value, and if an acknowledge signal is sent at maximum power, the acknowledge signal can reliably reach the wireless blood glucose meter 2 even in a situation in which the wireless blood glucose meter 2 and the portable terminal 3 are farther apart than normal, or in which there is an obstruction or the like between the wireless blood glucose meter 2 and the portable terminal 3, so that the radio waves are attenuated more than expected along the way. Consequently, there will be no cases in which an acknowledge signal cannot be received at the wireless blood glucose meter 2 even though the data was sent properly from the wireless blood glucose meter 2 to the portable terminal 3, and this prevents the wireless blood glucose meter 2 from deciding that the data was not sent properly and resending the data.

Other Embodiments

Embodiments of the present invention were described above, but the present invention is not limited to or by the above embodiments, and various modifications are possible without departing from the gist of the invention.

(A)

In the above embodiment, a case of application to the wireless blood glucose meter 2 was described as an example of a biological sample measurement apparatus, but the present invention is not limited to this.

For instance, the measurement apparatus may be one that measures lactic acid, uric acid, or the like, and as long as it is an apparatus that wirelessly transmits this data to another terminal or the like, the effect will be the same as that with the wireless blood glucose meter 2 pertaining to the above embodiment.

(B)

With the wireless blood glucose meter 2 in the above embodiment, an example was given in which the condition for extracting history information was extracting history information for the same day of the week and the same time period as during measurement, but the present invention is not limited to this.

For instance, the condition may be such that extraction is performed in the order of newest to oldest, or may be such that extraction is performed on the same day of the week and in the same time period as during measurement and from the newest entry. Suitably setting the extraction condition (the transmission power determination rule) allows it to be matched to the usage conditions of the person using the wireless blood glucose meter.

(C)

With the wireless blood glucose meter 2 in the above embodiment, an example was given in which the transmission power control circuit 251 switched the transmission power selector 253 so that a value 2 dBm less than or greater than the latest transmission power would be outputted according to the history information, but the present invention is not limited to this.

For instance, the transmission power control circuit may switch the transmission power selector so that a value 3 dBm less than or greater than the latest transmission power is outputted, and the amount by which the value is greater or less does not matter. The value can be set to a suitable range as desired.

(D)

With the wireless blood glucose meter 2 in the first embodiment above, an example was given in which the power computation circuit 255 determined the transmission power so that the noise ratio of the noise power register 256 to the transmission power, according to the history information and the measured noise, would be 0.9 times, 1.0 times, and 1.1 times the noise ratio of the noise power to the transmission power of the most recent history information, but the present invention is not limited to this.

For instance, the noise ratio adjusted by the reception power selector 255 may be adjusted so that the result is 0.8 times, 1.0 times, and 1.2 times, and this adjustment ratio is not that important. The adjustment ratio can be set to a suitable range as desired.

(E)

With the wireless blood glucose meter 2 in the above-mentioned third embodiment, an example was given in which the transmission power control circuit 251 switched the reception power selector 255 so as to set to a value that is 2 dBm less than or greater than the reference reception power currently stored, according to the history information, but the present invention is not limited to this.

For instance, the transmission power control circuit may switch the reception power selector so as to set to a value 3 dBm less than or greater than the reference reception power that has been set, and the amount by which the value is greater or less does not matter. The value can be set to a suitable range as desired.

(F)

With the wireless blood glucose meter 2 in the above embodiments, an example was given in which the transmission power control circuit 251 checked whether or not the blood glucose level was at least 400 mg/dL when blood glucose level data and an actuation pulse were outputted from the blood glucose level detector 21, but the present invention is not limited to this.

This number is nothing but a common index used by diabetes patients, and may instead be set to a value of 350 mg/dL, for example, as dictated by the user.

Also, the alarm sound output component 263 and the display component 262 emitted an alarm if the measured blood glucose level was 50 mg/dL or less, but here again these may be set as dictated by the user.

(G)

With the wireless blood glucose meter 2 in the above embodiments, an example was given in which the control blocks shown in FIG. 1 were each constructed from a hardware function, but the present invention is not limited to this.

The construction of the control blocks shown in FIG. 1 may, for example, comprise a single piece of hardware or computer software, or hardware and computer software functions may be combined, and this may be suitably determined according to the processing capability and so forth.

INDUSTRIAL APPLICABILITY

The biological sample measurement apparatus pertaining to the present invention affords less power consumption in communication using weak radio waves, and is useful as a biological sample measurement apparatus that performs wireless communication using a battery as its power supply.

The invention claimed is:

1. A biological sample measurement apparatus for communicating wirelessly with an external device, comprising:
    a biological data measurement component for measuring biological data;
    a transmitter for transmitting the biological data measured by the biological data measurement component;
    a receiver for receiving an acknowledge signal that is returned when the external device has properly received the biological data transmitted by the transmitter;
    a storage component for storing as history information whether or not the acknowledge signal was received and transmission power when the transmitter transmitted the biological data; and
    a transmission power determiner for determining transmission power of the transmitter on the basis of the history information stored in the storage component, or the history information extracted according to a transmission power determination rule that sets forth extraction conditions.

2. The biological sample measurement apparatus according to claim 1,
    wherein the transmission power determiner extracts a specific number of pieces of the history information according to the transmission power determination rule, and determines the transmission power of the transmitter so that the transmission power of the transmitter is lower than the transmission power stored as the history information, when the extracted history information includes at least a specific number of pieces of the history information for which the acknowledge signal has been received.

3. The biological sample measurement apparatus according to claim 1,
    wherein the transmission power determiner extracts a specific number of pieces of the history information according to the transmission power determination rule, and determines the transmission power of the transmitter so that the transmission power of the transmitter is higher than the transmission power stored as the history information, when the extracted history information does not include at least a specific number of pieces of the history information for which the acknowledge signal has been received.

4. The biological sample measurement apparatus according to claim 1,
    further comprising a noise power measurement component for measuring noise power just before the transmitter transmits,
    wherein the storage component further stores as the history information the noise power measured by the noise power measurement component.

5. The biological sample measurement apparatus according to claim 4,
    wherein the transmission power determiner extracts the history information for which the acknowledge signal has been received according to the transmission power determination rule, and determines the transmission power of the transmitter on the basis of the noise power measured by the noise power measurement component, so that a ratio of the measured noise power to the transmission power of the transmitter is the same as a ratio of the noise power to the transmission power in the extracted history information.

6. The biological sample measurement apparatus according to claim 4,
    wherein the transmission power determiner extracts a specific number of pieces of the history information according to the transmission power determination rule, and determines the transmission power of the transmitter on the basis of the noise power measured by the noise power measurement component, so that a ratio of the measured noise power to the transmission power of the transmitter is greater than the ratio of the noise power to the transmission power in the history information, when the extracted history information includes at least a specific number of pieces of the history information for which the acknowledge signal has been received.

7. The biological sample measurement apparatus according to claim 4,
    wherein the transmission power determiner extracts a specific number of pieces of the history information according to the transmission power determination rule, and determines the transmission power of the transmitter with respect to the noise power measured by the noise power measurement component, so that a ratio of the measured noise power to the transmission power of the transmitter is less than the ratio of the noise power to the transmission power in the history information, when the extracted history information does not include at least a specific number of pieces of the history information for which the acknowledge signal has been received.

8. The biological sample measurement apparatus according to claim 1,
    wherein the transmission power determination rule is set up so as to extract the history information for the same day of the week as when the history information is extracted by the transmission power determiner.

9. The biological sample measurement apparatus according to claim 1,
    wherein the transmission power determination rule is set up so as to extract the history information of the same time period as when the history information is extracted by the transmission power determiner.

10. The biological sample measurement apparatus according to claim 1, wherein the transmission power determiner determines the maximum transmission power which the transmitter is able to output if the biological data measured by the biological data measurement component is not a value within a specific range.

11. The biological sample measurement apparatus according to claim 1,
further comprising an interface having a display component for displaying the biological data measured by the biological data measurement component, an operating setting component for allowing the user to make various operating settings, and an alarm sound output component for outputting an alarm sound,
wherein, if the biological data measured by the biological data measurement component is lower than a specific value, an alarm sound is outputted from the alarm sound output component, and an emergency status is displayed on the display component.

12. A biological sample measurement apparatus for communicating wirelessly with an external device, comprising:
a biological data measurement component for measuring biological data;
a transmitter for transmitting the biological data measured by the biological data measurement component;
a receiver for receiving an acknowledge signal that is returned when the external device has properly received the biological data transmitted by the transmitter;
a storage component for storing a reference reception power that is the optimal reception power when the external device receives the biological data, and history information that includes whether or not the acknowledge signal was received, transmission power when the transmitter transmitted the biological data, and reception power when the external device has received the biological data; and
a transmission power determiner for determining transmission power when the transmitter transmits on the basis of the history information and the reference reception power stored in the storage component, or the history information extracted according to a transmission power determination rule that sets forth extraction conditions and the reference reception power.

13. The biological sample measurement apparatus according to claim 12,
wherein the transmission power determiner extracts one piece of the history information according to the transmission power determination rule, and compares the reception power in the extracted history information with the reference reception power, and if the reception power is higher, the transmission power when the transmitter transmits is determined so as to be lower than the transmission power stored as the extracted history information, and if the reception power is lower, the transmission power when the transmitter transmits is determined so as to be higher than the transmission power stored as the extracted history information.

14. The biological sample measurement apparatus according to claim 12,
wherein the transmission power determiner extracts a specific number of pieces of the history information according to the transmission power determination rule, and if the extracted history information includes at least a specific number of pieces of the history information for which the acknowledge signal has been received, the reference reception power is set lower than the value stored in the storage component.

15. The biological sample measurement apparatus according to claim 12,
wherein the transmission power determiner extracts a specific number of pieces of the history information according to the transmission power determination rule, and if the extracted history information does not include at least a specific number of pieces of the history information for which the acknowledge signal has been received, the reference reception power is set higher than the value stored in the storage component.

16. The biological sample measurement apparatus according to claim 12,
wherein the transmission power determination rule is set up so as to extract the history information for the same day of the week as when the history information is extracted by the transmission power determiner.

17. The biological sample measurement apparatus according to claim 12,
wherein the transmission power determination rule is set up so as to extract the history information of the same time period as when the history information is extracted by the transmission power determiner.

18. The biological sample measurement apparatus according to claim 12,
wherein the transmission power determiner determines the maximum transmission power which the transmitter is able to output if the biological data measured by the biological data measurement component is not a value within a specific range.

19. The biological sample measurement apparatus according to claim 12,
further comprising an interface having a display component for displaying the biological data measured by the biological data measurement component, an operating setting component for allowing the user to make various operating settings, and an alarm sound output component for outputting an alarm sound,
wherein, if the biological data measured by the biological data measurement component is lower than a specific value, an alarm sound is outputted from the alarm sound output component, and an emergency status is displayed on the display component.

20. A biological sample measurement system, comprising:
a biological sample measurement apparatus having a biological data measurement component for measuring biological data, a transmitter for transmitting the biological data measured by the biological data measurement component, a receiver for receiving an acknowledge signal that is returned when the biological data transmitted by the transmitter has been properly received, a storage component for storing a reference reception power that is the optimal reception power when the external device receives the biological data, and history information that includes whether or not the acknowledge signal was received, transmission power when the transmitter transmitted the biological data, and reception power when the biological data has been received; and a transmission power determiner for determining transmission power when the transmitter transmits on the basis of the history information and the reference reception power stored in the storage component, or the history information extracted according to a transmission power determination rule that sets forth extraction conditions and the reference reception power; and
an external device having an external receiver for receiving biological data transmitted from the biological sample measurement apparatus, an error detector for determining whether or not the external receiver has properly received the biological data, an external transmitter for transmitting an acknowledge signal to the biological sample measurement apparatus when the error detector has determined that the biological data has been properly received, a reception power determiner for measuring the reception power when the external receiver has received the biological data and comparing this with a specific value, and a transmission power selector for selecting the transmission power of the external transmitter on the basis of the determination result of the reception power determiner.

21. The biological sample measurement system according to claim 20,
  wherein the transmission power selector selects the maximum power as the transmission power in the external transmitter when the reception power determiner has determined that the reception power when the biological data has been received by the external receiver is lower than the specific value.

22. The biological sample measurement system according to claim 16,
  wherein the transmission power determination rule is set up so as to extract the history information for the same day of the week as when the history information is extracted by the transmission power determiner.

23. The biological sample measurement system according to claim 16,
  wherein the transmission power determination rule is set up so as to extract the history information of the same time period as when the history information is extracted by the transmission power determiner.

24. The biological sample measurement system according to claim 16,
  wherein the transmission power determiner determines the maximum transmission power which the transmitter is able to output if the biological data measured by the biological data measurement component is not a value within a specific range.

25. The biological sample measurement system according to claim 16,
  further comprising an interface having a display component for displaying the biological data measured by the biological data measurement component, an operating setting component for allowing the user to make various operating settings, and an alarm sound output component for outputting an alarm sound,
  wherein, if the biological data measured by the biological data measurement component is lower than a specific value, an alarm sound is outputted from the alarm sound output component, and an emergency status is displayed on the display component.

* * * * *